US011446319B2

(12) United States Patent
Moriwaki et al.

(10) Patent No.: US 11,446,319 B2
(45) Date of Patent: Sep. 20, 2022

(54) COMPOSITION CONTAINING FLAVONOID-CYCLODEXTRIN CLATHRATE COMPOUND

(71) Applicants: Masamitsu Moriwaki, Suzuka (JP); Kentaro Kumoi, Yokohama (JP); Ryo Nakagawa, Yokkaichi (JP); Miki Sagisaka, Okazaki (JP); Makoto Ozeki, Suzuka (JP)

(72) Inventors: Masamitsu Moriwaki, Suzuka (JP); Kentaro Kumoi, Yokohama (JP); Ryo Nakagawa, Yokkaichi (JP); Miki Sagisaka, Okazaki (JP); Makoto Ozeki, Suzuka (JP)

(73) Assignee: TAIYO KAGAKU CO., LTD., Yokkaichi (JP)

( * ) Notice: Subject to any disclaimer, the term of this patent is extended or adjusted under 35 U.S.C. 154(b) by 0 days.

(21) Appl. No.: 17/056,552

(22) PCT Filed: Oct. 3, 2018

(86) PCT No.: PCT/JP2018/037055
§ 371 (c)(1),
(2) Date: Nov. 18, 2020

(87) PCT Pub. No.: WO2019/230013
PCT Pub. Date: Dec. 5, 2019

(65) Prior Publication Data
US 2021/0205344 A1    Jul. 8, 2021

(30) Foreign Application Priority Data
Jun. 1, 2018   (JP) .............................. JP2018-105800

(51) Int. Cl.
*A61K 31/7048*   (2006.01)
*A61K 47/69*   (2017.01)
*A61K 8/60*   (2006.01)
*A61K 8/73*   (2006.01)
*A23L 29/30*   (2016.01)
*A23L 33/105*   (2016.01)
*A23L 27/00*   (2016.01)
*A23L 5/41*   (2016.01)
*A23L 2/60*   (2006.01)

(52) U.S. Cl.
CPC ............ *A61K 31/7048* (2013.01); *A23L 2/60* (2013.01); *A23L 5/41* (2016.08); *A23L 27/84* (2016.08); *A23L 27/86* (2016.08); *A23L 29/35* (2016.08); *A23L 29/37* (2016.08); *A23L 33/105* (2016.08); *A61K 8/602* (2013.01); *A61K 8/738* (2013.01); *A61K 47/6951* (2017.08); *A23V 2002/00* (2013.01); *A61K 2800/10* (2013.01); *A61K 2800/524* (2013.01); *A61K 2800/56* (2013.01)

(58) Field of Classification Search
CPC .... A61K 31/7048; A61K 8/602; A61K 8/738; A61K 47/6951; A61K 2800/56; A61K 2800/10; A61K 2800/524; A23L 29/37; A23L 29/35; A23L 27/84; A23L 33/105; A23L 27/86; A23L 5/41; A23L 2/60
USPC ........................................................ 514/127
See application file for complete search history.

(56) References Cited

U.S. PATENT DOCUMENTS

| | | | |
|---|---|---|---|
| 5,445,842 | A | 8/1995 | Tanaka et al. |
| 5,756,543 | A | 5/1998 | Katsuragi et al. |
| 5,847,108 | A | 12/1998 | Kanaoka et al. |
| 2008/0187622 | A1 | 8/2008 | Moriwaki et al. |
| 2010/0166897 | A1 | 7/2010 | Laboureau et al. |
| 2012/0083460 | A1 | 4/2012 | Emura et al. |
| 2015/0272184 | A1 | 10/2015 | John et al. |
| 2019/0248825 | A1 | 8/2019 | Moriwaki et al. |
| 2020/0062796 | A1 | 2/2020 | Moriwaki et al. |

FOREIGN PATENT DOCUMENTS

| | | |
|---|---|---|
| JP | 2-283246 A | 11/1990 |
| JP | 6-248194 A | 9/1994 |
| JP | 7-107972 A | 4/1995 |
| JP | 3208113 B2 | 9/2001 |
| JP | 3419958 B2 | 6/2003 |
| JP | 2003-183166 A | 7/2003 |
| JP | 2003-261593 A | 9/2003 |

(Continued)

OTHER PUBLICATIONS

Yousuf et al, Carbohydrate Research, 2013, 365, 46-51.*

(Continued)

*Primary Examiner* — Ganapathy Krishnan
(74) *Attorney, Agent, or Firm* — Birch, Stewart, Kolasch & Birch, LLP

(57) ABSTRACT

A composition containing one or more materials selected from the group consisting of fatty acids, proteins, peptides, amino acids, vitamins, minerals, alcohols, sweeteners, acidulants, antioxidants, thickening stabilizer, and surfactants, and a flavonoid-cyclodextrin inclusion compound, wherein the inclusion compound contains an inclusion compound obtained by treating a flavonoid having a rhamnoside structure with an enzyme having rhamnosidase activity in the presence of a cyclodextrin. According to the present invention, the bitterness and the changes in color tones originated from flavonoids can be inhibited, and foodstuff or the like having an unpleasant taste can be improved, so that the present invention can be suitably utilized in fields such as medicaments, foodstuff, health foods, foods for specified health use, and cosmetics.

21 Claims, No Drawings

(56) References Cited

FOREIGN PATENT DOCUMENTS

| | | | |
|---|---|---|---|
| JP | 2006-75064 A | 3/2006 | |
| JP | 2006-115772 A | 5/2006 | |
| JP | 2006-182777 A | 7/2006 | |
| JP | 2006182777 | * | 7/2006 |
| JP | 2008-271836 A | 11/2008 | |
| JP | 2008-271839 A | 11/2008 | |
| JP | 2008-271839 A | * | 11/2008 |
| JP | 2008271836 | * | 11/2008 |
| JP | 2008271839 A | * | 11/2008 |
| JP | 4457067 B2 | 4/2010 | |
| JP | 5256370 B2 | 8/2013 | |
| JP | 5259149 B2 | 8/2013 | |
| JP | 5298232 B2 | 9/2013 | |
| JP | 2013-215155 A | 10/2013 | |
| JP | 5552400 B2 | 7/2014 | |
| JP | 2015-65943 A | 4/2015 | |
| JP | 2015-188450 A | 11/2015 | |
| JP | 2015-208241 A | 11/2015 | |
| JP | 2016-7147 A | 1/2016 | |
| JP | 2017-63742 A | 4/2017 | |
| JP | 6186104 B2 | 8/2017 | |
| JP | 6421280 B1 | 11/2018 | |
| WO | WO 2005/030975 A1 | 4/2005 | |
| WO | WO 2010/110328 A1 | 9/2010 | |

OTHER PUBLICATIONS

Dwyer et al, Am J Clin Nutr, 2013, 3(98suppl), 1611s-1618S.*
Mandalari et al, J. Agric. Food Chem 2006, 54, 8307-8313.*
International Search Report (PCT/ISA/210) issued in PCT/JP2018/037055 dated Jan. 8, 2019.
Japanese Office Action for application No. 2019-510716 dated Apr. 9, 2019.
Japanese Office Action for application No. 2019-510716 dated Aug. 5, 2019.
Japanese Office Action for application No. 2019-510716 dated Oct. 29, 2019.
Extended European Search Report for European Application No. 18920645.1, dated Feb. 7, 2022.

* cited by examiner

COMPOSITION CONTAINING FLAVONOID-CYCLODEXTRIN CLATHRATE COMPOUND

TECHNICAL FIELD

The present invention relates to a composition containing a flavonoid-cyclodextrin inclusion compound, foodstuff, medicament, or cosmetics (foodstuff or the like) containing the composition, and a method for producing foodstuff or the like, a method for inhibiting bitterness originated from a flavonoid in the foodstuff or the like, a method for inhibiting changes in color tones originated from a flavonoid, a method for inhibiting an unpleasant taste, and a method for improving cosmetics on skin.

BACKGROUND ART

Flavonoids such as catechin, rutin, isoquercitrin, quercetin, hesperidin, hesperetin-7-glucoside, naringenin-7-glucoside, enzymatically treated isoquercitrin, enzymatically treated hesperidin, and isoflavone have been known to have physiological activities in anti-obesity, anti-inflammatory actions, anti-allergy, anti-hypertension, anti-osteoporosis, reduction in body fats, and the like.

However, when a flavonoid is contained in foodstuff or a medicament, one may undesirably taste its bitterness even when a content of the flavonoid is slight. For this reason, reports have been made for inhibiting the bitterness.

For example, a flavonoid with bitterness that is included by a cyclodextrin has been reportedly allowed to reduce its bitterness. For example, bitterness of a catechin-containing composition has been reportedly reduced by a combined use of β-cyclodextrin and γ-cyclodextrin with the catechin-containing composition. (Patent Publication 1)

Bitterness, acerbity, and astringency of isoflavone derivatives (malonyl daidzein, malonyl genistein, etc.) have been reportedly inhibited by inclusion of an isoflavone derivative by β-cyclodextrin or γ-cyclodextrin. (Patent Publication 2)

A combination of a glycosylation product of the flavonoid glycoside with a diacyl glycerol remarkably reduces bitterness, acerbity, or acidity of the glycosylation product of the flavonoid glycoside, to provide flavorful fat-and-oil containing foods; and a method for inhibiting acerbity or astringency of naringin, characterized by adding 0.001 to 2 parts by weight of sucralose, based on 1 part by weight of naringin showing acerbity or astringency, have been disclosed. (Patent Publications 3 and 4)

In order to reduce bitterness or acidity particularly caused when an isoquercitrin and a glycoside thereof ("enzymatically treated isoquercitrin") are used at high concentrations, and to significantly improve its lingering taste, the containment of one or more members of edible acids, fatty acids, sugars, sugar alcohols, alcohols, antioxidants, high-intensity sweeteners, proteins, peptides, amino acids, vitamins, minerals, thickening stabilizers, and surfactants has been disclosed. (Patent Publication 5)

In addition, since a flavonoid is generally more likely to be oxidized, when foodstuff, medicaments, cosmetics or the like containing a flavonoid are stored for a long period of time, the coloration progresses gradually so that the color tones may undergo great changes. Therefore, reports have been made to control color tones.

For example, a quercetin glycoside-formulated container-packed beverage which is less likely to undergo changes in color tones even when stored for a long period of time by blending an antioxidant having absorption in a wavelength region of from 300 to 420 nm in a beverage blended with a quercetin glycoside, and making adjustments so that the chroma of the beverage is from 26 to 45 has been proposed. (Patent Publication 6)

A container-packed beverage which is less likely to undergo changes in color tones by containment of a specified amount of an aliphatic alcohol, erythritol, xylitol, maltitol, trehalose, or the like to a specified amount of an isoquercitrin and a glycosylation product thereof has been proposed. (Patent Publications 7 and 8)

In addition, eating or drinking is limited due to an unpleasant taste such as lingering sweet taste, sweetness, bitterness, acerbity, acidity, or acidic taste (acidity) of foodstuff. Therefore, these unpleasant tastes have been demanded to be improved and reduced. For example, a hesperidin glycoside or a mixture of a hesperidin glycoside and a hesperidin, and a dispersed hesperetin that are effective in improvements in flavors of undesirable foodstuff (Patent Publications 9 and 10), and a taste improving agent for inhibiting bitterness, spiciness, acerbity, acridity, and astringency of foods other than soft candies, oral medicaments, or cosmetics, characterized in that the agent contains a metal salt or an amino acid salt of an ester between monoglyceride or diglyceride and a polycarboxylic acid (Patent Publication 11) have been disclosed.

In addition, improvements in bitterness, acerbity, or astringency of various materials by a cyclodextrin have been disclosed. For example, addition of a cyclodextrin in order to improve bitterness of a casein hydrolyzed product, and in order to improve bitterness of peptides; and granules in which a cyclodextrin is added in order to mask bitterness and unpleasant taste of crude medicines have been proposed. (Patent Publications 12 to 14)

In addition, in order to improve food having unpleasant tastes such as bitterness and acerbity, a taste modifying agent containing one or more members of enzymatically treated isoquercitrins, which is a flavonoid, and cyclic dextrins, has been published. (Patent Publication 15)

In addition, for cosmetic use of skins, a combination of a monosaccharide and an antioxidant such as a flavonoid has been published. (Patent Publication 16)

PRIOR ART REFERENCES

Patent Publications

Patent Publication 1: Japanese Patent Laid-Open No. 2006-115772
Patent Publication 2: Japanese Patent Laid-Open No. 2003-183166
Patent Publication 3: Japanese Patent No. 4457067
Patent Publication 4: Japanese Patent No. 5259149
Patent Publication 5: Japanese Patent Laid-Open No. 2015-208241
Patent Publication 6: Japanese Patent Laid-Open No. 2015-65943
Patent Publication 7: Japanese Patent No. 5256370
Patent Publication 8: Japanese Patent No. 5298232
Patent Publication 9: Japanese Patent No. 3208113
Patent Publication 10: Japanese Patent Laid-Open No. 2016-07147
Patent Publication 11: Japanese Patent No. 3419958
Patent Publication 12: Japanese Patent Laid-Open No. Hei-2-283246
Patent Publication 13: Japanese Patent Laid-Open No. 2006-75064
Patent Publication 14: Japanese Patent No. 5552400

Patent Publication 15: Japanese Patent Laid-Open No. 2017-63742

Patent Publication 16: Japanese Patent No. 6186104

SUMMARY OF THE INVENTION

Problems to be Solved by the Invention

As mentioned above, although various proposal have been made on a method for inhibiting bitterness originated from flavonoids, a method for improving color tones originated from flavonoids, a method for improving an unpleasant taste by the containment of a specified material, and a method for improving cosmetics on skin, those methods are not satisfactory, so that further improvements are desired.

An object of the present inventions is to provide a flavonoid-containing composition in which bitterness and changes in color tones are inhibited. Another object is to provide foodstuff or the like containing the composition and a method for production thereof. Another object is to provide a new method for inhibiting bitterness in foodstuff or the like, a method for inhibiting changes in color tones, a method for inhibiting an unpleasant taste, and a method for improving cosmetics on skin.

Means to Solve the Problems

The present invention relates to the following [1] to [7]:
[1] A composition containing one or more materials selected from the group consisting of fatty acids, proteins, peptides, amino acids, vitamins, minerals, alcohols, sweeteners, acidulants, antioxidants, thickening stabilizers, and surfactants, and a flavonoid-cyclodextrin inclusion compound, wherein the inclusion compound contains an inclusion compound obtained by treating a flavonoid having a rhamnose structure with an enzyme having rhamnosidase activity in the presence of a cyclodextrin.
[2] Foodstuff containing a composition as defined in [1].
[3] A medicament containing a composition as defined in [1].
[4] Cosmetics containing a composition as defined in [1].
[5] A method for producing foodstuff, a medicament, or cosmetics, including mixing foodstuff raw materials, medicament raw materials, or cosmetic raw materials with a composition as defined in [1].
[6] A method for inhibiting bitterness originated from a flavonoid in foodstuff or a medicament, including mixing foodstuff raw materials or medicament raw materials with a composition as defined in [1].
[7] A method for inhibiting changes in color tones originated from a flavonoid in foodstuff, a medicament, or cosmetics, including mixing foodstuff raw materials, medicament raw materials, or cosmetic raw materials with a composition as defined in [1].

Effects of the Invention

According to the present invention, a flavonoid-containing composition in which bitterness and changes in color tones are inhibited can be provided. Also, foodstuff containing the composition and a method for production thereof can be provided. Also, a new method for inhibiting bitterness in foodstuff or the like, a method for inhibiting changes in color tones, a method for inhibiting an unpleasant taste, and a method for improving cosmetics on skin can be provided. Here, the improving (improvement in) cosmetics as referred to in the present invention refers to an increase in viability in skin cells by protecting skin cells against sunlight and increasing a reproducible strength, thereby reducing occurrences of wrinkles and improving skin complexions or the like.

MODES FOR CARRYING OUT THE INVENTION

As a result of studying the above objects, the present inventors have found that bitterness and changes in color tones originated from a flavonoid are inhibited by a composition containing a specified material and an inclusion compound in which a flavonoid is included by a cyclic oligosaccharide (hereinafter simply referred to as "inclusion compound"). Further, the inhibition of an unpleasant taste such as lingering sweet taste, sweetness, bitterness, acerbity, acridity, or acidity caused due to the containment of a particular material, and the exhibition of the effects of improving cosmetics on skin have been found.

The composition of the present invention contains a material given below and an inclusion compound.

The material includes fatty acids, proteins, peptides, amino acids, vitamins, minerals, alcohols, sweeteners, acidulants, antioxidants, thickening stabilizers, and surfactants. In the composition of the present invention, one or more materials can be contained.

The fatty acid is not particularly limited so long as the fatty acid is usable for foodstuff or the like, which includes, for example, caproic acid, caprylic acid, pelargonic acid, capric acid, lauric acid, myristic acid, pentadecylic acid, palmitic acid, palmitoleic acid, stearic acid, oleic acid, vaccenic acid, linoleic acid, α-linolenic acid, β-linolenic acid, dihomo-γ-linolenic acid, arachidonic acid, lignoceric acid, nervonic acid, 9-tetradecenoic acid, 9-pentadecenoic acid, docosahexaenoic acid, eicosapentaenoic acid, and the like.

The protein is not particularly limited so long as the protein is usable for foodstuff or the like, which includes, for example, gelatins, collagens, caseins, casein sodium, casein phosphopeptides, whey proteins, lactoferrin, soybean proteins, wheat gluten, polyglutamic acids, and the like.

The peptide is not particularly limited so long as the peptide is usable for foodstuff or the like, which includes, for example, degradation products of the above proteins, and the like.

The amino acid is not particularly limited so long as the amino acid is usable for foodstuff or the like, which includes, for example, alanine, arginine, asparagine, aspartic acid, cysteine, glutamine, glutamic acid, glycine, valine, histidine, isoleucine, leucine, lysine, threonine, methionine, phenylalanine, proline, serine, threonine, tryptophan, tyrosine, valine, theanine, and the like.

The vitamin is not particularly limited so long as the vitamin is usable for foodstuff or the like, which include, for example, vitamin A, vitamin B1, vitamin B2, niacin, pantothenic acid, vitamin B6, vitamin B12, biotin, ascorbic acid (vitamin C), vitamin D2, vitamin D3, vitamin E, vitamin K, folic acid, and the like. Among them, ascorbic acid is preferred, from the viewpoint of inhibiting bitterness and changes in color tones of the flavonoid, and from the viewpoint of more improving an unpleasant taste such as acidity in the food or foodstuff containing vitamins.

The mineral is not particularly limited so long as the mineral is usable for foodstuff or the like, which includes, for example, sodium, potassium, calcium, iron, magnesium, copper, manganese, zinc, selenium, phosphorus, iodine, chromium, molybdenum, and the like.

The alcohol is not particularly limited so long as the alcohol is usable for foodstuff or the like, which include, for example, flavor-containing alcohol components such as monohydric alcohols such as methanol, ethanol, 1-propanol, isopropanol, 1-butanol, 2-butanol, isobutanol, isoamyl alcohol, 2-pentanol, 3-pentanol, 1-hexanol, 2-hexanol, 3-hexanol, 1-heptanol, 2-heptanol, 3-heptanol, and 4-heptanol; and polyhydric alcohols such as ethylene glycol, propylene glycol, 1,3-butanediol, and propylene glycol, and the like.

The sweetener is not particularly limited so long as the sweetener supplies sweetness and is usable for foodstuff or the like, which includes, for example, sugars, sugar alcohols, and high-intensity sweeteners. The sugar includes, for example, monosaccharides such as fructose, glucose, rhamnose, tagatose, and arabinose; disaccharides such as lactose, trehalose, maltose, and sucrose; polysaccharides such as dried glucose syrup; oligosaccharides such as malto-oligosaccharides and galacto-oligosaccharides; starch syrup, honey, and the like. The sugar alcohol includes, for example, sorbitol, erythritol, xylitol, maltitol, lactitol, mannitol, threitol, arabitol, ribitol, reduced starch syrup, reduced palatinose, and the like. The high-intensity sweeteners include, for example, aspartame, sucralose, acesulfame potassium, advantame, saccharin, neotame, thaumatin, monellin, monatin, monk fruit extracts, licorice extracts, glycyrrhizin, *Stevia* extracts, *Stevia* enzymatically treated products, Rebaudioside A, stevioside, glycyrrhizin, Mabinlin, Brazzein, and the like. Among them, aspartame, sucralose, acesulfame potassium, *Stevia* extracts, sorbitol, erythritol, and xylitol are preferred, from the viewpoint of more inhibiting bitterness and changes in color tones of the flavonoid, and from the viewpoint of more improving a lingering sweet taste, or an unpleasant sweet taste in the food and foodstuff containing a sweetener. In addition, rhamnose is preferred, from the viewpoint of more inhibiting a lingering metallic taste and/or a lingering acidic taste of a flavonoid, and from the viewpoint of the cosmetic effects on skin.

The acidulant is not particularly limited so long as the acidulant supplies acidity and is usable for foodstuff or the like, which includes, for example, adipic acid, butyric acid, isobutyric acid, citric acid, gluconic acid, succinic acid, formic acid, acetic acid, tartaric acid, lactic acid, phytic acid, fumaric acid, malic acid, propionic acid, 4-hydroxybenzoic acid, 2,5-dihydroxybenzoic acid, 3,4-dihydroxybenzoic acid, vanillic acid, 4-hydroxy-3,5-dimethoxybenzoic acid, and polyphosphoric acid, pyrophosphoric acid, metaphosphoric acid, phosphoric acid or salts thereof, and the like.

The antioxidant is not particularly limited so long as the antioxidant is usable for foodstuff or the like, which includes, for example, erythorbic acid, sulfites, tocopherols, dibutylhydroxytoluene (BHT), butylhydroxyanisole (BHA), ethylenediaminetetraacetic acid, gallic acid compounds, licorice oily extracts, edible *Canna* extracts, clove extracts, sage extracts, tempeh extracts, sauraceous extracts, raw coffee bean extracts, chlorogenic acid, sunflower seed extracts, grape seed extracts, blueberry leaf extracts, propolis extracts, gingko extracts, bayberry extracts, myricitrin, *Eucalyptus* leaf extracts, rosemary extracts, clove extracts, enzymatically treated rutin, enzymatically treated isoquercitrin, isoflavone, taxifolin (dihydroquercetin), catechin, polymerized catechin, tea extracts, nobiletin, methoxyflavone, coenzyme Q10, apple extracts, enzymatically decomposed apple extracts, sesame oil extracts, rice bran oil extracts, tannin, caffeine, and oxides of these antioxidants, for example, dehydroascorbic acid, oxides of erythorbic acid, tocopherol oxide, and the like. Among them, catechin, tea extracts, chlorogenic acid, tannin or caffeine is preferred, from the viewpoint of more exhibiting effects on an unpleasant taste such as bitterness, acerbity, or acridity, in the food and foodstuff containing an antioxidant.

The thickening stabilizer is not particularly limited so long as the thickening stabilizer is usable for foodstuff or the like, which include, for example, pullulan, dextran, curdlan, gellan gum, xanthan gum, β-glucan, guar gum, guar gum enzyme decomposate, locust bean gum, tamarind seed gum, linseed gum, dammar gum, gum arabic, arabinogalactan, gum ghatti, carrageenan, agar, agarose, fucoidan, alginic acid, pectin, soybean polysaccharides, chitin, chitosan, chitosan oligosaccharide, glucosamine, konjac powder, glucomannan, cellulose, carboxymethyl cellulose sodium, carboxymethyl cellulose calcium, hydroxypropyl cellulose, hydroxypropylmethyl cellulose, fermented celluloses, starches, hydroxypropyl starches, dextrin, maltodextrin, hyaluronic acid, polyglutamic acid, and the like.

The surfactant is not particularly limited so long as the surfactant is usable for foodstuff or the like, which includes, for example, sorbitol fatty acid esters, polysorbitol fatty acid esters, organic acid monoglycerides, sorbitan fatty acid esters, propylene glycol fatty acid esters, lecithins, enzymatically decomposed lecithins, resolecithins, soybean lecithins, egg yolk lecithins, sucrose fatty acid esters, saponin, quillai saponin, and the like.

The content of the material in the composition of the present invention is preferably 0.001% by mass or more, more preferably 0.003% by mass or more, and even more preferably 0.005% by mass or more, from the viewpoint of inhibiting bitterness and change in color tones, and the content is preferably 80% by mass or less, more preferably 75% by mass or less, and even more preferably 70% by mass or less, from the viewpoint of influences to tastes and color tones. In addition, the content of the material in the composition of the present invention is preferably 0.01% or more, and more preferably 0.02% by mass or more, from the viewpoint of improving an unpleasant taste of the material, and the upper limit is not particularly limited so long as it is a concentration showing an unpleasant taste, and preferably 90% or less. Here, the content in a case where two or more kinds of the materials are contained refers to a total amount of the materials.

In addition, in a case where a rhamnose is contained as a material, a molar ratio of a rhamnose to a flavonoid inclusion compound (rhamnose/flavonoid) is preferably 0.05 or more, more preferably 0.1 or more, even more preferably 0.5 or more, and even more preferably 0.8 or more, from the viewpoint of inhibiting a lingering metallic taste and/or a lingering acidic taste of the flavonoid, and from the viewpoint of the cosmetic effects on skin, and the molar ratio is preferably 20 or less, more preferably 15 or less, even more preferably 10 or less, and even more preferably 1.2 or less, from the viewpoint of tastes, and from the viewpoint of skin cosmetics.

The flavonoid in the inclusion compound is a flavonoid without a rhamnoside structure, which includes, for example, isoquercitrin, hesperetin-7-glucoside, naringenin-7-glucoside (prunin), diosmetin-7-glucoside, myricetin, eriodictyol-7-glucoside, luteolin-7-glucoside, delphinidin-3-glucoside, cyanidin-3-glucoside, isorhamnetin-3-glucoside, kaempferol-3-glucoside, apigenin-7-glucoside, quercetin, hesperetin, naringenin, acacetin-7-glucoside, daidzein, genistein, glycitein, daidzin, genistin, glycitin, and derivatives thereof. The derivatives include acetylated products, malonylated products, and methylated products. Among them, isoquercitrin, hesperetin-7-gluco side, and naringenin-7-glucoside are preferred, from the viewpoint of more inhibiting bitterness and changes in color tones of the flavonoid, and from the viewpoint of more improving foodstuff and medicaments having an unpleasant taste, and from the viewpoint of the cosmetic effects on skin by cosmetic articles, or the like.

The cyclic oligosaccharides in the inclusion compound are compounds in which monosaccharides are connected in a ring form, which include, for example, cyclodextrin, cyclodextran, cyclofructan, cycloalternan, cluster dextrin, and the like. Among them, cyclodextrin and cyclodextran are preferred, and cyclodextrin is more preferred, from the viewpoint of inhibiting bitterness and changes in color tones of the flavonoid, and from the viewpoint of more improving foodstuff and medicaments having an unpleasant taste, and from the viewpoint of the cosmetic effects on skin by cosmetic articles, or the like.

The cyclodextrins (CD) are not limited in the kinds, including α-cyclodextrin (α-CD), branched cyclodextrin, and the like, and one or more members selected from the group consisting of β-cyclodextrin (β-CD), branched β-cyclodextrin (branched β-CD), and γ-cyclodextrin (γ-CD) can be preferably used.

The cyclodextrin is one kind of a cyclic oligosaccharide in which D-glucoses are bonded via an α-1,4-glycoside bond to form a cyclic structure, and those in which seven glucoses are bonded are β-cyclodextrin and those in which eight glucoses are bonded are γ-cyclodextrin. The branched β-CD is one in which one or more glucose residues, galactosyl groups or hydroxypropyl groups are linked to β-CD as a side chain, which includes maltosyl β-CD (G2-β-CD), hydroxypropyl-β-CD (HP-β-CD), and the like.

The molar ratio of the cyclodextrin to the flavonoid in the inclusion compound (cyclodextrin/flavonoid) is preferably 1.0 or more, more preferably 1.1 or more, and even more preferably 1.2 or more, from the viewpoint of stability, and the molar ratio is preferably 3.0 or less, more preferably 2.0 or less, and even more preferably 1.8 or less, from the viewpoint of bitterness, influences on color tones, and economic advantages.

As the inclusion compounds, various combinations of the above flavonoids and cyclic oligosaccharides may be contemplated. From the viewpoint of inhibiting bitterness, changes in color tones, and flavors of the flavonoid, and from the viewpoint of improving foodstuff and medicaments that have unpleasant tastes, and from the viewpoint of the cosmetic effects on skin by cosmetic articles, or the like, one or more members selected from the group consisting of isoquercitrin-γ-cyclodextrin inclusion compounds, hesperetin-7-glucoside-β-cyclodextrin inclusion compounds, and naringenin-β-cyclodextrin inclusion compounds are contained, wherein a molar ratio of a cyclodextrin to a flavonoid (isoquercitrin, hesperetin-7-glucoside, naringenin-7-glucoside, etc.) (cyclodextrin/flavonoid) is preferably from 1.0 to 3.0, and more preferably from 1.0 to 1.8.

In addition, from the viewpoint of inhibiting bitterness and changes in color tones of the flavonoid, and from the viewpoint of improving foodstuff and medicaments that have unpleasant tastes, and from the viewpoint of the cosmetic effects on skin by cosmetic articles, or the like, inclusion compounds obtained by an enzyme method described later are preferred. Although this mechanism is not elucidated, when an inclusion compound is prepared from a flavonoid glycoside and a cyclodextrin by stir-mixing (dissolution method, kneading method, or the like), the sites of the flavonoid glycosides (for example, rutin, etc.) that are included by cyclodextrin according to a dissolution method are randomly included in A-C ring, B ring, and glycoside moiety of the flavonoid glycoside (*PLOS ONE,* 10(3), e0120858, 2015). However, when an inclusion compound is prepared according to an enzyme method, the bonding sites and the ratios of the flavonoid glycosides included by a cyclodextrin are different from those of a dissolution method, so that the effects of inhibiting bitterness and changes in color tones, the effects of improving unpleasant tastes, and the cosmetic effects on skin would be more stronger.

The solubility of the flavonoid moiety in the inclusion compound in water is preferably 0.001% or more, more preferably 0.005% or more, even more preferably 0.01% or more, even more preferably 0.015% or more, even more preferably 0.02% or more, even more preferably 1.0% or more, even more preferably 2.0% or more, even more preferably 2.5% or more, and even more preferably 3% or more, from the viewpoint of inhibiting bitterness and changes in color tones of the flavonoid, and from the viewpoint of improving foodstuff and medicaments that have unpleasant tastes, and from the viewpoint of the cosmetic effects on skin by cosmetic articles, or the like. In addition, the upper limit can be, but not particularly limited to, for example, 20% or less. Here, the solubility of the flavonoid moiety in water as used herein is a percent concentration by mass at 25° C., which can be measured in accordance with a method described in Examples set forth below.

The content of the inclusion compound, as indicated on the basis of the content of the flavonoid in the inclusion compound, is such that the flavonoid in the composition of the present invention is preferably an amount of 0.001% by mass or more, more preferably an amount of 0.005% by mass or more, and even more preferably an amount of 0.01% by mass or more. The content is preferably an amount of 10% by mass or less, more preferably an amount of 9% by mass or less, and even more preferably an amount of 8% by mass or less, from the viewpoint of inhibiting bitterness and changes in color tones of the flavonoid, and from the viewpoint of the cosmetic effects on skin by cosmetic articles or the like. In addition, the content is preferably an amount of 10% by mass or less, more preferably an amount of 1% by mass or less, and even more preferably an amount of 0.1% by mass or less, from the viewpoint of improving the composition having an unpleasant taste. Here, when the inclusion compounds are contained in two or more kinds, the content is a total amount of the flavonoids in the inclusion compounds.

The composition of the present invention can further optionally contain additives such as perfumes (including emulsified perfumes), foaming agents, foam stabilizers, various esters, pigments (natural pigments (anthocyanin pigments, carotenoid pigments, etc.), synthetic pigments), emulsifiers, preservatives, seasonings, carbonates, organic acids, dietary fibers, fruit juices, grain (crop) extracts, malt extracts, vegetable extracts, honey or nectar extracts, tea extracts, black tea extracts, root vegetable extracts, green vegetable extracts, moringa extracts, amla extract, and quality stabilizers, alone or in a combination of two or more kinds. Here, the content of the additives can be properly selected within the range that would not impair the object of the present invention.

The composition of the present invention has excellent effects of inhibiting bitterness and changes in color tones of the flavonoid and effects of improving an unpleasant taste of foodstuff or the like, in addition to various physiological effects such as antioxidant effects and radical capturing effects, so that the composition can be suitably used as a composition for foodstuff, a composition for medicaments, a composition for cosmetics, and a composition for foodstuff additives. More specifically, the composition can be used as a material for inhibiting brown discoloration of foodstuff or the like, ultraviolet absorption, antioxidation, anti-allergy, anticancer, anti-inflammation, improvement in intestinal flora, deodorization, suppression of plasma cholesterol elevation, suppression of blood pressure elevation, suppression of blood sugar elevation, suppression of platelet aggregation, prevention of dementia, combustion of body fat, suppression of body fat accumulation, improvement in staying power, anti-fatigue, improvement in sensitivity to cold, improvement of skin conditions, hair restoration, suppression of amyotrophy, sleeping, anticancer, anti-virus, cosmetic whitening, skin improvement, or unwrinkling, and the composition can also be used as an antioxidant, a fading preventive, a deterioration preventive for flavor for foodstuff additives. The composition for foodstuff additives is added for deterioration prevention of a sweetener, a colorant, a preservative, a thickening stabilizer, a color developing agent, a bleaching agent, a mildewproof agent, a gum base, a bittering agent, a lustering agent, an acidulant, a seasoning, an emulsifying agent, a reinforcing agent, an agent for production, a flavor, or the like, and can be provided in the form of a mixed formulation.

In other words, in the present invention, foodstuff, medicaments, cosmetics or the like each containing a composition of the present invention can be provided. These foodstuff or the like can be prepared by a method for production including mixing foodstuff raw materials, medicament raw materials, or cosmetic raw materials with a composition of the present invention. In addition, in the present invention, a method for inhibiting bitterness originated from a flavonoid in foodstuff or medicaments, including mixing foodstuff raw materials or medicament raw materials with a composition of the present invention, and a method for inhibiting changes in color tones originated from a flavonoid in foodstuff, medicaments, or cosmetics, including mixing foodstuff raw materials, medicament raw materials, or cosmetic raw materials with a composition of the present invention. Here, in the step of mixing raw materials of foodstuff or the like with a composition of the present invention, the composition of the present invention may be added to raw materials of foodstuff or the like, or a material and an inclusion compound may be separately added to the raw materials of foodstuff or the like.

The foodstuff include foods and beverages, which include, for example, nutrient supplements, health foods, foods for specified health use, foods with function claims, foods for diet therapy, comprehensive health foods, supplements, tea beverages, coffee beverages, juices, refreshing beverages, health drinks, and the like.

The medicament includes drugs or quasi-drugs, and the medicaments are preferably oral formulations or dermally externally applicable agents, and can be in the form of solution, tablet, granule, capsule, syrup, lotion, spray-dried agent, or ointment.

The cosmetics can be in the form of cream, liquid lotion, milky emulsion lotion, spray, lotion, or the like.

The content of the composition of the present invention in a case where the foodstuff or the like are in the form of liquid or semi-solid is such that the content of the flavonoid in the composition of the present invention is preferably in an amount of 0.0001% by mass or more, more preferably in an amount of 0.001% by mass or more, and even more preferably in an amount of 0.01% by mass or more, from the viewpoint of inhibiting bitterness and changes in color tones of the flavonoid, and from the viewpoint of improving an unpleasant taste of foodstuff or the like, and from the viewpoint of the cosmetic effects on skin by cosmetic articles, or the like. The content is preferably in an amount of 5% by mass or less, more preferably in an amount of 2% by mass or less, and even more preferably 1% by mass or less, from the viewpoint of inhibiting bitterness and changes in color tones, and from the viewpoint of improving an unpleasant taste of foodstuff or the like, and from the viewpoint of the cosmetic effects on skin by cosmetic articles, or the like.

The content of the composition of the present invention in a case where the foodstuff or the like are in the form of solid is such that the content of the flavonoid in the composition of the present invention is preferably in an amount of 0.001% by mass or more, more preferably in an amount of 0.01% by mass or more, even more preferably in an amount of 0.015% by mass or more, and even more preferably in an amount of 0.02% by mass or more, from the viewpoint of inhibiting bitterness of the flavonoid and changes in color tones, and from the viewpoint of improving an unpleasant taste of foodstuff or the like, and from the viewpoint of the cosmetic effects on skin by cosmetic articles, or the like. The content is preferably in an amount of 30% by mass or less, more preferably in an amount of 25% by mass or less, even more preferably in an amount of 20% by mass or less, and even more preferably 10% by mass or less, from the viewpoint of inhibiting bitterness of the flavonoid and changes in color tones, and from the viewpoint of improving an unpleasant taste of foodstuff or the like, and from the viewpoint of the cosmetic effects on skin by cosmetic articles, or the like.

Next, the method for producing a composition of the present invention will be described. The composition of the present invention can be obtained by mixing raw materials, an inclusion compound, and optional additives by a known method.

The method for preparing an inclusion compound contained in the composition of the present invention is not particularly limited, and an inclusion compound can be prepared by a known method such as an emulsification method, a saturated aqueous solution method, a kneading method, a dissolution method, or a blend-and-pulverizing method. An inclusion compound which is prepared by an enzyme method given below is preferred, from the viewpoint of inhibiting bitterness of the flavonoid and changes in color tones, and from the viewpoint of improving an unpleasant taste of foodstuff or the like, and from the viewpoint of the cosmetic effects on skin by cosmetic articles, or the like. Here, in the following explanation, an embodiment where a cyclodextrin is used is taken as an example, but the present invention is not construed to be limited thereto, and other cyclic oligosaccharides can be used in the same manner.

A preferred method for preparing an inclusion compound includes a method of treating a flavonoid having a rhamnoside structure with an enzyme having rhamnosidase activity in the presence of a cyclodextrin (hereinafter also referred to as "enzyme method"). According to the enzyme method, a rhamnose is cleaved from a flavonoid having a rhamnoside structure to obtain an inclusion compound of a flavonoid without a rhamnoside structure and a cyclodextrin.

The enzyme method can be carried out while allowing materials to stand in a solvent such as water, or while stirring, and in order to inhibit oxidization or brown discoloration in the reaction, the air in a headspace of a reaction system may be replaced with an inert gas such as nitrogen, or an antioxidant such as ascorbic acid may also be added to a reaction system. The enzyme reaction can be terminated by a known method such as a method of deactivating enzymes by heating a liquid reaction mixture. After the termination of the enzyme reaction, a reaction mixture that is filtered, purified to remove a rhamnose or the like and dried is a dried product of an inclusion compound.

Here, in the present invention, a composition containing a rhamnose prepared from a liquid prepared by filtering a preparation liquid after the cleaving step, or one subsequently powdered with a spray-dryer, or freeze-drying or the like is referred to as "a composition containing a flavonoid inclusion compound," and a liquid from which a rhamnose is removed by dialysis, or with a resin or the like, or a dried product thereof is described as "a flavonoid inclusion compound."

In the enzyme method, the flavonoid having a rhamnoside structure used as a raw material includes ones selected from flavones, flavonols, flavanones, flavanols, and isoflavones each having a rhamnoside structure. The flavonoid includes, for example, rutin, hesperidin, naringin, diosmin, eriocitrin, myricitrin, neohesperidin, luteolin-7-rutinoside, delphinidin-3-rutinoside, cyanidin-3-rutinoside, isorhamnetin-3-rutinoside, kaempferol-3-rutinoside, acacetin-7-rutinoside, derivatives thereof and the like, and plant extracts such as cassis extracts, ginkgo leaf extracts, and citrous extracts, each containing a flavonoid listed can be used as raw materials. In addition, the derivatives include acetylated products, malonylated products, methylated products, and the like.

In the enzyme method, the amount of the cyclodextrin to be present in the reaction system is, but not particularly limited to, preferably from 0.01 to 60% by mass, more preferably from 1 to 50% by mass, and even more preferably from 3 to 40% by mass. The amount when two or more cyclodextrins are used refers to a total amount thereof.

In the enzyme method, a molar ratio of a cyclodextrin to be present to a flavonoid having a rhamnoside structure (cyclodextrin to be present/flavonoid) is preferably 0.01 or more, more preferably 0.9 or more, and even more preferably 1.0 or more, from the viewpoint of efficiencies, economic advantages, and influences to tastes, and the molar ratio is preferably 10.0 or less, more preferably 6.0 or less, even more preferably 4.0 or less, and even more preferably 3.0 or less, from the viewpoint of economic advantages.

In the enzyme method, the enzyme having a rhamnosidase activity is not limited in its origin, and any one of those originated from animals, from plants, and from microorganisms can be used. Further, the enzyme may be a genetically recombinant enzyme. In addition, the form of the enzyme is not particularly limited. Specific examples of the enzyme having a rhamnosidase activity include a hepseridinase, a naringinase, a β-glucosidase, a pectinase, and the like. The amount of the enzyme having a rhamnosidase activity used may differ depending upon the kinds of the enzyme used, the reaction conditions, the kinds of the raw material flavonoid having a rhamnoside structure, and the like. For example, when the enzyme is a hepseridinase, a naringinase, or a β-glucosidase, it is preferable that the amount used is from 0.01 to 1000 U based on 1 g of the flavonoid having a rhamnoside structure. As the reaction conditions, a reaction temperature and a pH of a liquid reaction mixture can be selected in accordance with the properties of the enzyme used, and a pH is preferably from 3 to 7, and more preferably a pH is preferably from 3.5 to 6.5. In addition, an enzyme reaction can also be carried out at a pH of 7 or less after dissolving a flavonoid having a rhamnoside structure in an alkaline region. The solvent used in a reaction system includes an aqueous medium. The aqueous medium as used herein refers to water or an aqueous solution of an organic solvent. Water is exemplified by tap water, distilled water, ion-exchanged water, and purified water. The organic solvent is not particularly limited, so long as the organic solvent is evenly miscible with water. The organic solvent is preferably ethanol, from the viewpoint that the organic solvent is applicable to foods or the like. In addition, the reaction temperature is preferably from 10° to 80° C., and more preferably from 40° to 75° C. In addition, the reaction time is varied depending upon the kinds of the enzymes or the like, and the reaction time can be, for example, from 1 to 100 hours, and preferably from 2 to 24 hours. The method for purification is not particularly limited, and the purification can be carried out by a resin treatment step (adsorption method, ion-exchanging method or the like), a membrane treatment step (ultrafiltration membrane treatment method, reverse osmosis membrane treatment method, zeta potential membrane treatment method or the like), electrodialysis method, salting out, acid precipitation, recrystallization, solvent fractionation method or the like.

The percent conversion of the inclusion compound produced by the enzyme method is preferably from 10 to 100%, more preferably from 40 to 100%, even more preferably from 70 to 100%, and even more preferably from 90 to 100%. The percent conversion, %, shows a percent conversion of a flavonoid having a rhamnoside structure to a flavonoid without a rhamnoside structure, which can be calculated by HPLC analysis by (Peak area of a flavonoid without a rhamnoside structure×100/(Peak area of a flavonoid having a rhamnoside structure+Peak area of a flavonoid without a rhamnoside structure).

Here, when unpurified, it is obtained as a composition containing besides the produced inclusion compound, a raw material flavonoid having a rhamnoside structure (for example, rutin, hesperidin, naringin, or the like), a flavonoid which may be contained in raw materials (for example, quercetin, kaempferol-3-rutinoside, kaempferol-3-glucoside, hesperetin, naringenin, or the like), a cleaved rhamnose, or the like. Also, in one embodiment of adding an inclusion compound in the preparation of the composition of the present invention, a composition containing a rhamnose mentioned above or the like and an inclusion compound can be added. In this case, a molar ratio of a rhamnose to a flavonoid in the inclusion compound in the composition of the present invention (rhamnose/flavonoid) is preferably from 0.1 to 10.0, and more preferably from 0.8 to 1.2.

EXAMPLES

The present invention will be more specifically described hereinbelow by way of Examples, without intending to limit the scope of the present invention to these Examples. Here, "%" means "% by mass," unless noted otherwise particularly.

<Solubility>

The dried products prepared were added to a 100 ml beaker containing 50 ml of water at 50° C. with stirring until the dried products were no longer dissolved and precipitated out. The liquid mixture was allowed to stand at room temperature (25° C.), 1 ml of the supernatant was then filtered, and an isoquercitrin concentration, a hesperetin-7-glucoside concentration, or a naringenin-7-glucoside concentration was calculated according to HPLC, to obtain solubility.

Preparation Example 1: Isoquercitrin

One-hundred grams of rutin (manufactured by Alps Pharmaceutical Ind. Co., Ltd.) was added to make 1000 L of an aqueous solution, and the solution was adjusted to 70° C. and a pH of 4.5. Thereafter, 0.3 g of a naringinase (Amano Enzyme Inc., 5000 u/g) was added thereto while stirring the solution, and the liquid mixture was subjected to an enzyme reaction for 24 hours. Thereafter, the precipitates were recovered, recrystallized and dried, to give 72 g of isoquercitrin having a content of 96% or more. It was confirmed that the product was identical to a reagent isoquercitrin (Wako) by the content and HPLC.

Preparation Example 2: Hesperetin-7-Glucoside

Seventy grams of hesperidin (manufactured by Hamari Chemicals, Ltd.) was added to make 1000 L of an aqueous solution, and the solution was adjusted to 70° C. and a pH of 4.5. Thereafter, 0.6 g of a naringinase (Amano Enzyme Inc., 5000 u/g) was added thereto while stirring the solution, and the liquid mixture was subjected to an enzyme reaction for 24 hours. Thereafter, the precipitates were recovered, recrystallized and dried, to give 42 g of hesperetin-7-glucoside having a content of 96% or more. It was confirmed that the product was identical to a reagent hesperetin-7-glucoside (Chem Faces) by the content and HPLC.

Preparation Example 3: Naringenin-7-Glucoside

Twenty grams of naringin (manufactured by SIGMA) was added to make 1 L of an aqueous solution, and the solution was adjusted to 70° C. and a pH of 4.5. Thereafter, 0.1 g of a naringinase (Amano Enzyme Inc., 5000 u/g) was added thereto while stirring the solution, and the liquid mixture was subjected to an enzyme reaction for 24 hours. Thereafter, the precipitates were recovered, recrystallized and dried, to give 12.6 g of naringenin-7-glucoside having a content of 96% or more. It was confirmed that the product was identical to a reagent naringenin-7-glucoside (Wako) by the content and HPLC.

Preparation Example 4: Isoquercitrin-γ-Cyclodextrin Inclusion Compound (Enzyme Method)

To 1000 ml beaker were added 80 g of the rutin and 170 g of a γ-cyclodextrin (Dexypearl γ-100, manufactured by PEARL ACE CORPORATION), and water was added thereto to make up an amount of 1000 g. The liquid mixture was adjusted to 70° C. and a pH of 4.5. Thereafter, 0.16 g of a naringinase (Amano Enzyme Inc., 5000 u/g) was added thereto while stirring the solution, and the liquid mixture was allowed to react for 24 hours. Having confirmed by HPLC analysis of a percent conversion of 96% or more, as calculated by ((Peak areas of isoquercitrin)×100/(Peak areas of rutin+Peak areas of isoquercitrin)), the reaction mixture was subjected to a filtration or dialysis to remove a rhamnose or the like, and a product was then spray-dried, to give 207 g of a dried product of an isoquercitrin-γ-cyclodextrin inclusion compound (a molar ratio of γ-cyclodextrin to isoquercitrin (γ-cyclodextrin/isoquercitrin) of 1.0) (isoquercitrin content: 26%). The solubility in water was 9.6%. The solubility was an isoquercitrin concentration analyzed from a concentration dissolved in distilled water at a room temperature of 25° C. by HPLC. Here, it was confirmed that the isoquercitrin was included by the γ-cyclodextrin with a differential-scanning calorimeter (DSC), nuclear magnetic resonance (NMR), and a Fourier transform infrared spectrometer (FT-IR).

Preparation Example 5: Isoquercitrin-γ-Cyclodextrin Inclusion Compound (Dissolution Method)

Four grams of the isoquercitrin and a γ-cyclodextrin (manufactured by PEARL ACE CORPORATION) were mixed at a molar ratio of 1:5 (a total mass of 60 g), and water was added thereto to make up a volume of 1000 ml. The liquid mixture was heated to about 85° C. and stirred for one hour, to dissolve solid components. Thereafter, the temperature was set back to room temperature, and a liquid mixture was filtered with a filter paper and then freeze-dried, to prepare 54 g of a powdery form of an isoquercitrin-γ-cyclodextrin inclusion compound. The solubility of isoquercitrin in water was 1.2%, which was a relatively low solubility as compared to that of the enzyme method of 9.6%. Here, in cases where molar ratios of 4 g of the isoquercitrin and a γ-cyclodextrin (manufactured by PEARL ACE CORPORATION) were changed to 1:1 to 4 in place of 1:5, the liquid mixtures were in a suspension state, and did not dissolve.

Preparation Example 6: Hesperetin-7-Glucoside-β-Cyclodextrin Inclusion Compound (Enzyme Method)

To 1000 ml beaker were added 30 g of the hesperidin and 84 g of a β-cyclodextrin (Dexypearl 13-100, manufactured by PEARL ACE CORPORATION), and water was added thereto to make up an amount of 1000 g. The liquid mixture was adjusted to 70° C. and a pH of 4.5. Thereafter, 0.16 g of a naringinase (Amano Enzyme Inc., 5000 u/g) was added thereto while stirring the solution, and the liquid mixture was allowed to react for 24 hours. It was confirmed by HPLC analysis that a percent conversion was 96% or more, as calculated by ((Peak areas of hesperetin-7-glucoside)×100/(Peak areas of hesperidin+Peak areas of hesperetin-7-glucoside)). Thereafter, the liquid mixture was subjected to filtration or dialysis to remove a rhamnose or the like, and a product was spray-dried, to give 93 g of an inclusion compound of the hesperetin-7-glucoside with the β-cyclodextrin (a molar ratio of β-cyclodextrin to hesperetin-7-glucoside (β-cyclodextrin/hesperetin-7-glucoside) of 1.5) (hesperetin-7-glucoside content: 21%). The solubility in water was 3.9%. The solubility was a hesperetin-7-glucoside concentration analyzed from a concentration dissolved in distilled water at a room temperature of 25° C. by HPLC. Here, it was confirmed that the hesperetin-7-glucoside was included by the β-cyclodextrin with a differential-scanning calorimeter (DSC), nuclear magnetic resonance (NMR), and a Fourier transform infrared spectrometer (FT-IR).

Preparation Example 7: Naringenin-7-Glucoside-β-Cyclodextrin Inclusion Compound (Enzyme Method)

To 1000 ml beaker were added 60 g of the naringin and 117 g of the β-cyclodextrin, and water was added thereto to make up an amount of 1000 g. The liquid mixture was adjusted to 70° C. and a pH of 4.5. Thereafter, 0.3 g of a naringinase (Amano Enzyme Inc., 5000 u/g) was added thereto while stirring the solution, and the liquid mixture was allowed to react for 24 hours. It was confirmed by HPLC analysis that a percent conversion was 96% or more, as calculated by ((Peak areas of naringenin-7-glucoside)×100/(Peak areas of naringin+Peak areas of naringenin-7-glucoside)). Thereafter, the liquid mixture was subjected to filtration, or dialysis to remove a rhamnose or the like, and a product was spray-dried, to give 142 g of an inclusion compound of naringenin-7-glucoside with the β-cyclodextrin (a molar ratio (β-cyclodextrin/naringenin-7-glucoside) of 1.0) (naringenin-7-glucoside content: 27%). The solubility in water was 9.2%. The solubility was a naringenin-7-glucoside concentration analyzed from a concentration dissolved in distilled water at a room temperature of 25° C. by HPLC. Here, it was confirmed that the naringenin-7-glucoside was included by the β-cyclodextrin with a differential-scanning calorimeter (DSC), nuclear magnetic resonance (NMR), and a Fourier transform infrared spectrometer (FT-IR).

Preparation Example 8: Composition Containing Isoquercitrin-γ-Cyclodextrin Inclusion Compound and Rhamnose—IQC Inclusion Compound-Containing Composition A product after the enzyme reaction was spray-dried without subjecting to dialysis in Preparation Example 4, to give a composition containing an isoquercitrin-γ-cyclodextrin inclusion compound and a rhamnose (220 g, isoquercitrin content: 24%). The molar ratio of a rhamnose to an isoquercitrin in the composition (rhamnose/isoquercitrin) was 1.0.

Preparation Example 9: Composition Containing Hesperetin-7-Glucoside-β-Cyclodextrin Inclusion Compound and Rhamnose—HPT-7G Inclusion Compound-Containing Composition A product after the enzyme reaction was spray-dried without subjecting to dialysis in Preparation Example 6, to give a composition containing a hesperetin-7-glucoside-β-cyclodextrin inclusion compound and a rhamnose (101 g, hesperetin-7-glucoside content: 20%). The molar ratio of a rhamnose to a hesperetin-7-glucoside in the composition (rhamnose/hesperetin-7-glucoside) was 1.0.

Preparation Example 10: Composition Containing Naringenin-7-Glucoside-β-Cyclodextrin Inclusion Compound and Rhamnose—NGN-7G Inclusion Compound-Containing Composition A product after the enzyme reaction was spray-dried without subjecting to dialysis in Preparation Example 7, to give a composition containing a naringenin-7-glucoside-β-cyclodextrin inclusion compound and a rhamnose (155 g, naringenin-7-glucoside content: 25%). The molar ratio of a rhamnose to a naringenin-7-glucoside in the composition (rhamnose/naringenin-7-glucoside) was 1.0.

Preparation Example 11: Isoquercitrin-γ-Cyclodextrin Inclusion Compound (Dissolution Method)
Four grams of the isoquercitrin and 11.5 g of a γ-cyclodextrin (manufactured by PEARL ACE CORPORATION) were mixed at a molar ratio (γ-cyclodextrin/isoquercitrin) of 1, and water was added thereto to make up a volume of 100 L (pH of 4, adjusted with citric acid). The liquid mixture was heated to about 85° C., and stirred for one hour, to dissolve solid components. Thereafter, the temperature was set back to room temperature, and the liquid mixture was filtered and concentrated, and then freeze-dried, to prepare 10.5 g of a powdery form of an isoquercitrin-γ-cyclodextrin inclusion compound (a molar ratio (γ-cyclodextrin/isoquercitrin) of 1, Preparation Example 11).

Here, even when 30 g of the isoquercitrin and 84 g of the γ-cyclodextrin were mixed at a molar ratio of 1, water was added thereto to make up a volume of 1 L (pH of 4, adjusted with citric acid), and a liquid mixture was heated to about 85° C., and stirred for one hour, the mixture was in a suspension state. Thereafter, the temperature was set back to room temperature, and the reaction mixture was filtered and concentrated, and then freeze-dried, to give 75 g of an isoquercitrin-γ-cyclodextrin inclusion compound having a molar ratio (γ-cyclodextrin/isoquercitrin) of 8.4.

Inclusion of the isoquercitrin by the γ-cyclodextrin and the molar ratios were confirmed with a differential-scanning calorimeter (DSC), nuclear magnetic resonance (NMR), a Fourier transform infrared spectrometer (FT-IR), and an HPLC saccharide analysis method.

Here, for comparisons, the flavonoid inclusion compounds prepared by the enzyme method were prepared by modifying the contents of the cyclodextrin during the enzyme reaction to have a molar ratio of a cyclodextrin to a flavonoid (cyclodextrin/flavonoid) of 1.5, 1.8, 2.0, 3.0 or the like.

(Method of Analyzing Flavonoid Concentration, Method of Calculating Flavonoid Content and Conversion Value)

Peak areas in accordance with the analysis of HPLC (SHIMADZU) (the conditions for HPLC:
column: CAPCELL PAK C18 SIZE 4.6 mm×250 mm (SHISEIDO), eluent: 20 to 40% (v/v) acetonitrile/0.1% aqueous phosphoric acid solution,
flow rate: 0.4 ml/min,
column temperature: 70° C.,
wavelengths: 351 nm (isoquercitrin), 280 nm (hesperetin-7-glucoside, naringenin-7-glucoside))
were compared to a calibration line drawn with each reagent (a reagent isoquercitrin (Wako), a reagent hesperetin-7-glucoside (Chem Faces), or a reagent naringenin-7-glucoside (Wako)), and a flavonoid concentration was calculated to calculate the flavonoid content in the beverages or the like of Examples. Here, with respect to the enzymatically treated isoquercitrin, the enzymatically treated hesperidin, and a dispersed hesperetin, the contents of the flavonoid moiety were indicated as conversion values. Specifically, the calculation was made as follows. Enzymatically treated isoquercitrin: An isoquercitrin conversion value was calculated by comparisons between a total sum of each of peak areas in accordance with the analysis of HPLC (under the same conditions as the analysis of the isoquercitrin concentration) and a peak area of a calibration curve of the reagent isoquercitrin.

Enzymatically treated hesperidin: A hesperetin-7-glucoside conversion value was calculated by comparisons between a total sum of each of peak areas in accordance with the analysis of HPLC (under the same conditions as the analysis of the hesperetin-7-glucoside concentration) and a peak area of a calibration curve of the reagent hesperetin-7-glucoside. Dispersed hesperetin: A hesperetin-7-glucoside conversion value was calculated by comparisons between an area in accordance with the analysis of HPLC (under the same conditions as the analysis of hesperetin-7-glucoside concentration) and a peak area of a calibration curve of the reagent hesperetin-7-glucoside.

(Method of Analyzing Molar Ratio of Rhamnose to Flavonoid (Rhamnose/Flavonoid))

A rhamnose content was measured using a composition containing a flavonoid inclusion compound and a rhamnose (HPLC saccharide analysis method (given below), a calibration curve drawn with rhamnose (Wako)), and a molar concentration of the rhamnose was then calculated. From a molar concentration of a flavonoid in an inclusion compound (calculated), a molar ratio of a rhamnose to a flavonoid (rhamnose/flavonoid) was calculated.

(HPLC Saccharide Analysis Method)

A calibration curve of a β-cyclodextrin (Wako) or a γ-cyclodextrin (Wako) was drawn in accordance with HPLC (SHIMADZU) analysis (the conditions of HPLC:
column: Inertsil NH2 (4.6×150 mm (GL Science, Inc.),
eluent: 65% acetonitrile/water (v/v),
detection: a differential refractometer RID-10A (SHIMADZU),
flow rate: 1 ml/min,
column temperature: 40° C.),
and a molar cyclodextrin concentration of a sample was then calculated, and molar ratios of cyclodextrin/isoquercitrin, cyclodextrin/hesperetin-7-glucoside, and cyclodextrin/naringenin-7-glucoside were calculated from molar concentrations of the isoquercitrin, the hesperetin-7-glucoside, and the naringenin-7-glucoside. Here, the molar ratio of the filtrate after the termination of the reaction was the same for the freeze-dried product.

1. Lemon Beverage: Improvement in Bitterness of Flavonoids

Example 1

A lemon beverage containing an isoquercitrin-γ-cyclodextrin inclusion compound of Preparation Example 4 in an amount of 0.007% by mass in terms of a content of isoquercitrin, and 0.005% by mass of sucralose (pH 3, 0.08% by mass of citric acid, 0.1% by mass of a lemon flavor (manufactured by T. HASEGAWA CO., LTD.), the pH being adjusted with trisodium citrate) was prepared.

Examples 2 to 6, Comparative Examples 1 to 25, Reference Examples 1 and 2

The same procedures as in Example 1 were carried out except that the kinds of the inclusion compound and the amount of the sucralose were the component and the amount as listed in Table 1.

The details of the components listed in Table 1 are as follows.

Sucralose: (manufactured by TATE & LYLE)
(1) IQC–γCD Inclusion Compound (Enzyme Method): An isoquercitrin-γ-cyclodextrin inclusion compound of Preparation Example 4
(2) IQC–γCD Inclusion Compound (Dissolution Method): An isoquercitrin-γ-cyclodextrin inclusion compound of Preparation Example 5
(3) IQC+γCD: Separately adding and mixing 0.007% by mass of isoquercitrin of Preparation Example 1 and 0.02% by mass of a γ-cyclodextrin (manufactured by PEARL ACE CORPORATION) to a beverage
(4) Enzymatically Treated IQC: An enzymatically treated isoquercitrin (SANMELIN AO-3000, manufactured by San-Ei Gen F. F. I., Inc., isoquercitrin conversion value: 7.2% by mass)
(5) IQC: Isoquercitrin of Preparation Example 1
(6) HPT-7G-βCD Inclusion Compound (Enzyme Method): Hesperetin-7-glucoside-β-cyclodextrin inclusion compound of Preparation Example 6
(7) Enzymatically Treated HSP: A transglycolated hesperidin (Hesperidin S, HAYASHIBARA CO., LTD., hesperidin conversion value: 82.7% by mass)
(8) Dispersed HPT: Dispersed hesperetin (Peretin-D, EZAKI GLICO CO., LTD., hesperetin conversion value: 85% by mass)
(9) HPT-7G: Hesperetin-7-glucoside of Preparation Example 2
(10) NGN-7G-βCD Inclusion Compound (Enzyme Method): Naringenin-7-glucoside-β-cyclodextrin inclusion compound of Preparation Example 7
(11) NGN-7-G: Naringenin-7-glucoside of Preparation Example 3

<Evaluation of Bitterness>

The sensory evaluation regarding the bitterness by the flavonoids of Examples 1 to 6, Comparative Examples 1 to 25, and Reference Examples 1 and 2 was made by 7 panelists in a five-score rank in accordance with the following criteria, and a mean score of total points was calculated. The results are shown in Table 1. The bitterness by the flavonoid was subjected to sensory evaluations comprehensively of bitterness, acerbity and an unpleasant lingering taste (lingering bitter or acerb taste or the like), and the comparisons were made with the components of the same kinds. Specifically, a relative evaluation was made by defining Comparative Example 5 containing only isoquercitrin as an evaluation score of 1 in the evaluation of the beverages containing any one of (1) to (5) of Table 1, or defining Comparative Example 9 containing only hesperetin-7-glucoside as an evaluation score of 1 in the evaluation of the beverages containing any one of (6) to (9), or defining Comparative Example 11 containing only naringenin-7-glucoside as an evaluation score of 1 in the evaluation of the beverages containing any one of (10) to (11). A lemon beverage in which only isoquercitrin, hesperetin-glucoside, or naringenin-7-glucoside was added in an amount of 0.0007% (an amount 1/10 of the amount of the flavonoid alone to a beverage) is defined as a rank 5.

(Evaluation Criteria)
1: Bitterness is the strongest among the components of the same kinds.
2: Bitterness is somewhat stronger but weaker than the rank 1.
3: Bitterness is improved to a certain level as compared to the rank 1.
4: Bitterness is improved as compared to the rank 1.
5: Bitterness is highly improved as compared to the rank 1.

TABLE 1

| | | Evaluation of Bitterness | | | | | |
|---|---|---|---|---|---|---|---|
| | | Sucralose Without Addition | | Sucralose 0.005% by mass | | Sucralose 0.014% by mass | |
| (1) IQC-γCD Inclusion Compound (Enzyme Method) | Comp. Ex. 1 | 2.5 | Ex. 1 | 3.8 | Ex. 4 | 4.2 | |
| (2) IQC-γCD Inclusion Compound (Dissolution Method) | Comp. Ex. 2 | 1.7 | Ref. Ex. 1 | 1.9 | Ref. Ex. 2 | 2.7 | |
| (3) IQC + γCD | Comp. Ex. 3 | 1.1 | Comp. Ex. 12 | 1.4 | Comp. Ex. 19 | 1.5 | |
| (4) Enzymatically Treated IQC | Comp. Ex. 4 | 1.5 | Comp. Ex. 13 | 1.6 | Comp. Ex. 20 | 2.2 | |
| (5) IQC | Comp. Ex. 5 | 1.0 | Comp. Ex. 14 | 1.3 | Comp. Ex. 21 | 1.4 | |
| (6) HPT-7G-βCD Inclusion Compound (Enzyme Method) | Comp. Ex. 6 | 2.1 | Ex. 2 | 3.9 | Ex. 5 | 4.1 | |
| (7) Enzymatically Treated HSP | Comp. Ex. 7 | 1.5 | Comp. Ex. 15 | 1.8 | Comp. Ex. 22 | 2.0 | |
| (8) Dispersed HPT | Comp. Ex. 8 | 1.4 | Comp. Ex. 16 | 1.7 | Comp. Ex. 23 | 2.5 | |
| (9) HPT-7G | Comp. Ex. 9 | 1.0 | Comp. Ex. 17 | 1.2 | Comp. Ex. 24 | 1.3 | |
| (10) NGN-7G-βCD Inclusion Compound (Enzyme Method) | Comp. Ex. 10 | 2.3 | Ex. 3 | 3.7 | Ex. 6 | 4.1 | |
| (11) NGN-7G | Comp. Ex. 11 | 1.0 | Comp. Ex. 18 | 1.2 | Comp. Ex. 25 | 1.6 | |

*In the table, (1) to (5) are each an amount 0.007% by mass in terms of a content of isoquercitrin or a conversion value; (6) to (9) are each an amount 0.007% by mass in terms of a content of hesperetin-7-glucoside or a conversion value; and (10) and (11) are each an amount 0.007% by mass in terms of a content of naringenin-7-glucoside or a conversion value.

As shown in Table 1, among the values of the beverages containing any one of (1) to (5), the evaluation of the beverage containing only isoquercitrin (Comparative Example 5) had a score of 1.0 showing the most bitter taste, and the evaluation of the beverage containing an isoquercitrin-cyclodextrin inclusion compound (enzyme method) and 0.014% of sucralose (Example 4) had a score of 4.2, showing the most improvement in bitterness. Among the beverages containing any one of (6) to (9), the evaluation of the beverage containing only hesperetin-7-glucoside (Comparative Example 9) had a score of 1.0 showing the most bitter taste, and the evaluation of the beverage containing a hesperetin-7-glucoside-cyclodextrin inclusion compound (enzyme method) and 0.014% of sucralose (Example 5) had a score of 4.1, showing the most improvement in bitterness. Among the beverages containing any one of (10) to (11), the evaluation of the beverage containing only naringenin-7-glucoside (Comparative Example 11) had a score of 1.0 showing the most bitter taste, and the evaluation of the beverage containing a naringenin-7-glucoside-cyclodextrin inclusion compound (enzyme method) and 0.014% of sucralose (Example 6) had a score of 4.1, showing the most improvement in bitterness. In addition, although the isoquercitrin-γ-cyclodextrin inclusion compound prepared by the dissolution method showed some reducing effects of bitterness, the sensory evaluation was low, as compared to those of the enzyme method. Here, the similar evaluations as in the sensory evaluation shown in (2) were made in the isoquercitrin-cyclodextrin inclusion compound (dissolution method) prepared in Preparation Example 11.

Here, similar evaluations were also made with those containing 0.013% by mass or 0.04% by mass of aspartame (manufactured by AJINOMOTO CO., INC., PAL SWEET), 0.02% by mass or 0.05% by mass of acesulfame K (manufactured by Nutrinova, Sunnette), 0.02% by mass or 0.06% by mass of a Stevia extract (manufactured by Toyo Sugar Refining Co., Ltd., Stevilose 90), 3% by mass or 8% by mass of erythritol (manufactured by B Food Science Co., Ltd., Erythritol F), 3% by mass or 9% by mass of sorbitol (manufactured by B Food Science Co., Ltd., Sorbitol SP), 2% by mass or 6% by mass of xylitol (manufactured by B Food Science Co., Ltd., Xylitol), or 0.03% by mass or 0.1% by mass of ascorbic acid (manufactured by FUSO CHEMICAL CO., LTD.), in place of 0.005% by mass or 0.014% by mass of sucralose.

In addition, the same sensory evaluation of bitterness was made at a molar ratio of a cyclodextrin to a flavonoid (cyclodextrin/flavonoid) of the flavonoid inclusion compound (enzyme method) of from 1.0 to 3.0. Here, the lemon flavor had the same sensory evaluation at a molar ratio of from 1.0 to 1.8, but the lemon flavor was weakened at a molar ratio exceeding 2.0.

In addition, the sensory evaluations were nearly the same even when the compositions obtained in Preparation Examples 8 to 10 were each used in place of the flavonoid inclusion compounds in Examples 1 to 6. Also, the same results were shown even in the beverage of which flavonoid content or conversion value was 0.02% by mass.

2. Acidic Beverages: Improvements in Changes in Color Tones by Long-Term Storage of Flavonoids

Example 11

An acidic beverage containing an isoquercitrin-γ-cyclodextrin compound of Preparation Example 4 in an amount of 0.007% by mass in terms of the content of an isoquercitrin, and 0.005% by mass of sucralose (pH 3, 0.08% of citric acid, the pH being adjusted with trisodium citrate) was prepared.

Examples 12 to 16, Comparative Examples 31 to 55, and Reference Examples 11 to 12

The same procedures as in Example 11 were carried out except that the kinds of the inclusion compounds and the amount of sucralose were those components and amounts as listed in Table 2.

The details of the components listed in Table 2 are the same as those of Table 1, except for those shown hereinbelow:

(12) HPT-7G+βCD: Separately adding and mixing 0.007% by mass of hesperetin-7-glucoside of Preparation Example 2 and 0.02% by mass of β-cyclodextrin (manufactured by PEARL ACE CORPORATION) to a beverage <Evaluation of Color Tones>

Color tones of each of Examples 11 to 16, Comparative Examples 31 to 55, and Reference Examples 11 to 12 immediately after the production and after a three-month storage at 37° C. were evaluated for the measurements of a value of L, a value of a, and a value of b of the Lab color space with a spectrophotometer (Cary60 UV-VIS, Software: Cary Win UV/Color, Agilent Technologies) by placing a sample in a quartz cell having an optical path length of 10 mm. From the value of L, the value of a, and the value of b of an acidic beverage immediately after the production and the value of L, the value of a, and the value of b of an acidic beverage after a 3-month storage at 37° C., ΔE was obtained in accordance with the following formula, and shown in Table 2.

$$\Delta E=(\Delta L^2\Delta a^2+\Delta b^2)^{0.5}$$

The components of the same kinds ((1) to (5), (6) to (9), and (10) to (11) of Table 2) were compared.

TABLE 2

| | | Evaluation of Color Tones | | | | | |
|---|---|---|---|---|---|---|---|
| | | Sucralose Without Addition | | Sucralose 0.005% by mass | | Sucralose 0.014% by mass | |
| (1) IQC-γCD Inclusion Compound (Enzyme Method) | Comp. Ex. 31 | 1.35 | Ex. 11 | 0.75 | Ex. 14 | 0.65 |
| (2) IQC-γCD Inclusion Compound (Dissolution Method) | Comp. Ex. 32 | 1.41 | Ref. Ex. 11 | 1.20 | Ref. Ex. 12 | 1.10 |
| (4) Enzymatically Treated IQC | Comp. Ex. 33 | 1.45 | Comp. Ex. 42 | 1.40 | Comp. Ex. 49 | 1.30 |
| (5) IQC | Comp. Ex. 34 | 2.12 | Comp. Ex. 43 | 1.95 | Comp. Ex. 50 | 1.80 |
| (6) HPT-7G-βCD Inclusion Compound (Enzyme Method) | Comp. Ex. 35 | 1.70 | Ex. 12 | 0.81 | Ex. 15 | 0.55 |
| (12) HPT-7G + βCD | Comp. Ex. 36 | 1.90 | Comp. Ex. 44 | 1.70 | Comp. Ex. 51 | 1.55 |
| (7) Enzymatically Treated HSP | Comp. Ex. 37 | 1.79 | Comp. Ex. 45 | 1.63 | Comp. Ex. 52 | 1.45 |
| (8) Dispersed HPT | Comp. Ex. 38 | 1.81 | Comp. Ex. 46 | 1.67 | Comp. Ex. 53 | 1.55 |
| (9) HPT-7G | Comp. Ex. 39 | 1.95 | Comp. Ex. 47 | 1.81 | Comp. Ex. 54 | 1.79 |
| (10) NGN-7G-βCD Inclusion Compound (Enzyme Method) | Comp. Ex. 40 | 1.55 | Ex. 13 | 0.78 | Ex. 16 | 0.52 |
| (11) NGN-7G | Comp. Ex. 41 | 1.78 | Comp. Ex. 48 | 1.72 | Comp. Ex. 55 | 1.68 |

*In the table, (1), (2), (4), and (5) are each an amount 0.007% by mass in terms of a content of isoquercitrin or a conversion value; (6) to (9) and (12) are each an amount 0.007% by mass in terms of a content of hesperetin-7-glucoside or a conversion value; and (10) and (11) are each an amount 0.007% by mass in terms of a content of naringenin-7-glucoside or a conversion value.

As shown in Table 2, the changes in color tones in the acidic beverages were improved by adding each of an isoquercitrin-γ-cyclodextrin inclusion compound, a hesperetin-7-glucoside-β-cyclodextrin inclusion compound, and a naringenin-7-glucoside-β-cyclodextrin inclusion compound, and a sucralose. As shown in Table 2, among the values of the beverages containing any one of (1) to (5), the beverage containing only isoquercitrin (Comparative Example 34) had a value of 2.12 showing the highest score, and the beverage containing an isoquercitrin-cyclodextrin inclusion compound (enzyme method) and 0.014% of sucralose (Example 14) had a value of 0.65, showing the smallest change in color tones. Among the values of the beverages containing any one of (6) to (9), the beverage containing only hesperetin-7-glucoside (Comparative Example 39) had a value of 1.95 showing the highest score, and the evaluation of the beverage containing a hesperetin-7-glucoside-cyclodextrin inclusion compound (enzyme method) and 0.014% of sucralose (Example 15) had a value of 0.55, showing the smallest change in color tones. Among the values of the beverages containing any one of (10) to (11), the evaluation of the beverage containing only naringenin-7-glucoside (Comparative Example 41) had a value of 1.78 showing the highest score, and the evaluation of the beverage containing a naringenin-7-glucoside-cyclodextrin inclusion compound (enzyme method) and 0.014% of sucralose (Example 16) had a value of 0.52, showing the smallest change in color tones. In addition, although the isoquercitrin-γ-cyclodextrin inclusion compound prepared by the dissolution method showed some improved effects in color tones, the extent thereof was weaker as compared to those of the enzyme method. Here, the same evaluation was made in the isoquercitrin-cyclodextrin inclusion compound (dissolution method) prepared in Preparation Example 11 as in the evaluation of the color tones by the dissolution method shown in (2).

Here, similar evaluations were also made with those containing 0.013% by mass or 0.04% by mass of aspartame (manufactured by AJINOMOTO CO., INC., PAL SWEET), 0.02% by mass or 0.05% by mass of acesulfame K (manufactured by Nutrinova, Sunnette), 2% by mass or 6% by mass of a Stevia extract (manufactured by Toyo Sugar Refining Co., Ltd., Stevilose 90), 3% by mass or 8% by mass of erythritol (manufactured by B Food Science Co., Ltd., Erythritol F), 3% by mass or 9% by mass of sorbitol (manufactured by B Food Science Co., Ltd., Sorbitol SP), 2% by mass or 6% by mass of xylitol (manufactured by B Food Science Co., Ltd., Xylitol), or 0.03% by mass or 0.1% by mass of ascorbic acid (manufactured by FUSO CHEMICAL CO., LTD.), in place of 0.005% by mass or 0.014% by mass of sucralose. In addition, nearly the same evaluation was made even when the molar ratios of cyclodextrin to a flavonoid (cyclodextrin/flavonoid) of the flavonoid (isoquercitrin, hesperetin-7-glucoside, or naringenin-7-glucoside) inclusion compound (enzyme method) were fluctuated to from 1.0 to 3.0. Here, the sensory evaluation was made with a flavonoid inclusion compound-containing composition containing a rhamnose. As a result, the evaluation score was increased by 0.1 to 0.2.

3. Tablet: Improvements in Bitterness and Color Tones of Flavonoids

Example 21

A mixture of an isoquercitrin-γ-cyclodextrin inclusion compound of Preparation Example 4 in an amount of 5% by mass in terms of the content of an isoquercitrin, 0.04% by mass of a sucralose, 0.5% by mass of fine silicon dioxide particles, 2.5% by mass of citric acid, and balance a crystalline cellulose was pressure-molded with a hydraulic pressing machine (manufactured by RIKEN SEIKO, and corresponding mortar and pestle at a pressure of 100 kg/cm$^2$, to produce a tablet having a diameter of 9 mm and a weight of 300 mg.

Examples 22 to 26, and Comparative Examples 61 to 87

The same procedures as in Example 21 were carried out except that the kinds of the inclusion compounds and the amount of sucralose were those components and amounts as listed in Table 3 or 4.

The details of the components listed in Table 3 or 4, expressed in % by mass of each component, are the same as those of Tables 1 and 2, except for those shown hereinbelow:

(13) NGN-7G+βCD: Separately adding and mixing 5% by mass of naringenin-7-glucoside of Preparation Example 3 and 13% by mass of a β-cyclodextrin (manufactured by PEARL ACE CORPORATION) to a tablet <Evaluation of Bitterness>

The sensory evaluation regarding the bitterness of Examples 21 to 26 and Comparative Examples 61 to 84 was made by with five panelists, and a mean score of total points was calculated. The results are shown in Table 3. Tablets containing components of the same kinds were compared in the same manner as in the lemon beverages, and the evaluation criteria were the same criteria as those of the lemon beverages. Here, the tablets in which two tablets were chewed up and swallowed were evaluated for bitterness.

Values of Lab of each of Examples 21 to 26 and Comparative Examples 61 to 64, 66 to 72, 74 to 79, and 81 to 87 immediately after the production and after a three-month storage at 37° C. were measured, and ΔE values calculated are shown in Table 4. Specifically, as the values of Lab, those tablets crushed with a mortar were dissolved in an acidic solution (pH 3.1, 0.08% of citric acid, being adjusted with trisodium citrate) so as to have the content of a flavonoid or a conversion value thereof of 0.01% by mass, the solution was filtered, and the values of Lab were then measured. The measurement method and the calculation method for ΔE values are the same as those for the acidic beverages.

TABLE 3

| | Evaluation of Bitterness | | | | | |
|---|---|---|---|---|---|---|
| | Sucralose Without Addition | | Sucralose 0.04% by mass | | Sucralose 0.2% by mass | |
| (1) IQC-γCD Inclusion Compound (Enzyme Method) | Comp. Ex. 61 | 2.3 | Ex. 21 | 3.3 | Ex. 24 | 3.9 |
| (4) Enzymatically Treated IQC | Comp. Ex. 62 | 1.3 | Comp. Ex. 71 | 1.5 | Comp. Ex. 78 | 2.2 |
| (5) IQC | Comp. Ex. 63 | 1.0 | Comp. Ex. 72 | 1.2 | Comp. Ex. 79 | 1.2 |
| (6) HPT-7G-βCD Inclusion Compound (Enzyme Method) | Comp. Ex. 64 | 2.8 | Ex. 22 | 3.5 | Ex. 25 | 3.8 |
| (12) HPT-7G + βCD | Comp. Ex. 65 | 1.5 | Comp. Ex. 73 | 1.8 | Comp. Ex. 80 | 2.1 |
| (7) Enzymatically Treated HSP | Comp. Ex. 66 | 1.5 | Comp. Ex. 74 | 1.7 | Comp. Ex. 81 | 2.2 |
| (8) Dispersed HPT | Comp. Ex. 67 | 1.3 | Comp. Ex. 75 | 1.7 | Comp. Ex. 82 | 1.9 |
| (9) HPT-7G | Comp. Ex. 68 | 1.0 | Comp. Ex. 76 | 1.5 | Comp. Ex. 83 | 1.3 |
| (10) NGN-7G-βCD Inclusion Compound (Enzyme Method) | Comp. Ex. 69 | 2.2 | Ex. 23 | 4.1 | Ex. 26 | 4.1 |
| (11) NGN-7G | Comp. Ex. 70 | 1.0 | Comp. Ex. 77 | 1.3 | Comp. Ex. 84 | 1.3 |

*In the table, (1), (4), and (5) are each an amount 5% by mass in terms of a content of isoquercitrin or a conversion value; (6) to (9) and (12) are each an amount 5% by mass in terms of a content of hesperetin-7-glucoside or a conversion value; and (10) and (11) are each an amount 5% by mass in terms of a content of naringenin-7-glucoside or a conversion value.

TABLE 4

| | Evaluation of Color Tones | | | | | |
|---|---|---|---|---|---|---|
| | Sucralose Without Addition | | Sucralose 0.04% by mass | | Sucralose 0.2% by mass | |
| (1) IQC-γCD Inclusion Compound (Enzyme Method) | Comp. Ex. 61 | 1.32 | Ex. 21 | 0.85 | Ex. 24 | 0.65 |
| (4) Enzymatically Treated IQC | Comp. Ex. 62 | 1.45 | Comp. Ex. 71 | 1.30 | Comp. Ex. 78 | 1.25 |
| (5) IQC | Comp. Ex. 63 | 1.55 | Comp. Ex. 72 | 1.45 | Comp. Ex. 79 | 1.3 |
| (6) HPT-7G-βCD Inclusion Compound (Enzyme Method) | Comp. Ex. 64 | 1.35 | Ex. 22 | 0.75 | Ex. 25 | 0.55 |
| (7) Enzymatically Treated HSP | Comp. Ex. 66 | 1.42 | Comp. Ex. 74 | 1.45 | Comp. Ex. 81 | 1.45 |
| (8) Dispersed HPT | Comp. Ex. 67 | 1.45 | Comp. Ex. 75 | 1.51 | Comp. Ex. 82 | 1.49 |
| (9) HPT-7G | Comp. Ex. 68 | 1.56 | Comp. Ex. 76 | 1.51 | Comp. Ex. 83 | 1.49 |
| (10) NGN-7G-βCD Inclusion Compound (Enzyme Method) | Comp. Ex. 69 | 1.33 | Ex. 23 | 0.68 | Ex. 26 | 0.42 |
| (13) NGN-7G + βCD | Comp. Ex. 85 | 1.45 | Comp. Ex. 86 | 1.20 | Comp. Ex. 87 | 1.15 |
| (11) NGN-7G | Comp. Ex. 70 | 1.52 | Comp. Ex. 77 | 1.48 | Comp. Ex. 84 | 1.43 |

*In the table, (1), (4), and (5) are each an amount 5% by mass in terms of a content of isoquercitrin or a conversion value; (6) to (9) are each an amount 5% by mass in terms of a content of hesperetin-7-glucoside or a conversion value; and (10), (11), and (13) are each an amount 5% by mass in terms of a content of naringenin-7-glucoside or a conversion value.

As shown in Tables 3 and 4, the bitterness and the changes in color tones were improved by adding an isoquercitrin-γ-cyclodextrin inclusion compound a hesperetin-7-glucoside-β-cyclodextrin inclusion compound, and a naringenin-7-glucoside-β-cyclodextrin inclusion compound and sucralose.

Here, similar evaluations were also made with those containing 0.1% by mass or 0.5% by mass of aspartame (manufactured by AJINOMOTO CO., INC., PAL SWEET), 0.14% by mass or 0.7% by mass of acesulfame K (manufactured by Nutrinova, Sunnette), 0.08% by mass or 0.2% by mass of a *Stevia* extract (manufactured by Toyo Sugar Refining Co., Ltd., Stevilose 90), 14% by mass or 70% by mass of erythritol (manufactured by B Food Science Co., Ltd., Erythritol F), 14% by mass or 70% by mass of sorbitol (manufactured by B Food Science Co., Ltd., Sorbitol SP), 14% by mass or 70% by mass of xylitol (manufactured by B Food Science Co., Ltd., Xylitol), or 0.2% by mass or 1% by mass of ascorbic acid (manufactured by FUSO CHEMICAL CO., LTD.), in place of 0.04% by mass or 0.2% by mass of the sucralose. In addition, nearly the same evaluation was made even when the molar ratios of a cyclodextrin to a flavonoid (cyclodextrin/flavonoid) of the flavonoid (isoquercitrin, hesperetin-7-glucoside, or naringenin-7-glucoside) inclusion compound (enzyme method) were fluctuated to from 1.0 to 3.0.

4. Black Tea Beverages: Improvements in Bitterness

Examples 31 to 33, and Comparative Examples 91 to 96

Raw materials as listed in Table 5 were stir-blended, and the mixture was then subjected to a total volume compensation. A flavor was added when the temperature reached at 93° C., and the mixture was subjected to hot-pack filling in a 350 mL PET bottle, to prepare a black tea beverage (pH 5).

The details of the components as listed in Table 5 are the same as Tables 1 to 4, except for those shown hereinbelow.
(14) IQC Inclusion Compound-Containing Composition: A composition containing an isoquercitrin-γ-cyclodextrin inclusion compound of Preparation Example 8 and a rhamnose
(15) HPT-7G Inclusion Compound-Containing Composition: A composition containing a hesperetin-7-glucoside-β-cyclodextrin inclusion compound of Preparation Example 9 and a rhamnose
(16) NGN-7G Inclusion Compound-Containing Composition: A composition containing a naringenin-7-glucoside-β-cyclodextrin inclusion compound of Preparation Example 10 and a rhamnose
Black tea extract: A black tea concentrate (manufactured by GS FOOD CO., LTD.)
Sodium hydrogencarbonate: (manufactured by Taiyo Pharmaceutical Co., LTD.)
*Stevia* extract: (manufactured by Toyo Sugar Refining Co., Ltd., Stevilose 90)
L-Ascorbic acid: (manufactured by FUSO CHEMICAL CO., LTD.)
Xylitol: (manufactured by B Food Science Co., Ltd.)
Black tea flavor: (manufactured by OGAWA Flavors & Flagrances Co., Ltd.)

<Evaluation of Bitterness>

The sensory evaluation regarding the bitterness of each of Examples 31 to 33 and Comparative Examples 91 to 96 was made by seven panelists in a three-rank evaluation in accordance with the following criteria, and a mean score of total points was calculated. The results are shown in Table 5. The bitterness was subjected to sensory evaluations comprehensively of bitterness, acerbity and an unpleasant lingering taste, and the components of the same kinds (Table 5 (Experimental Example 31, Comparative Example 91, and Comparative Example 92) (Experimental Example 32, Comparative Example 93, Comparative Example 94, and Comparative Example 95) (Comparative Example 33, Comparative Example 96)) were compared. Since the black tea beverages of Comparative Examples 92, 95, or 96 containing only isoquercitrin, hesperetin-7-glucoside, or naringenin-7-glucoside had the strongest bitterness in the comparisons of the components of the same kinds, the evaluation thereof was a rank 1, and the evaluation in which the amount of isoquercitrin, hesperetin-7-glucoside, or naringenin-7-glucoside only was 1/10 was a rank 3.

(Evaluation Criteria)
1: Bitterness is the strongest among the components of the same kinds.
2: Bitterness is improved as compared to the rank 1.
3: Bitterness is highly improved as compared to the rank 1.

TABLE 5

|  | Ex. 31 | Comp. Ex. 91 | Comp. Ex. 92 | Ex. 32 | Comp. Ex. 93 | Comp. Ex. 94 | Comp. Ex. 95 | Ex. 33 | Comp. Ex. 96 |
| --- | --- | --- | --- | --- | --- | --- | --- | --- | --- |
| Black tea extract, % by mass | 18.6 | 18.6 | 18.6 | 18.6 | 18.6 | 18.6 | 18.6 | 18.6 | 18.6 |
| Sodium hydrogencarbonate, % by mass | 0.002 | 0.002 | 0.002 | 0.002 | 0.002 | 0.002 | 0.002 | 0.002 | 0.002 |
| (14) IQC Inclusion Compound-Containing Composition | 0.01 | 0 | 0 | 0 | 0 | 0 | 0 | 0 | 0 |
| (4) Enzymatically Treated IQC | 0 | 0.01 | 0 | 0 | 0 | 0 | 0 | 0 | 0 |
| (5) IQC | 0 | 0 | 0.01 | 0 | 0 | 0 | 0 | 0 | 0 |
| (15) HPT-7G Inclusion Compound-Containing Composition | 0 | 0 | 0 | 0.01 | 0 | 0 | 0 | 0 | 0 |
| (7) Enzymatically Treated HSP | 0 | 0 | 0 | 0 | 0.01 | 0 | 0 | 0 | 0 |
| (8) Dispersed HPT | 0 | 0 | 0 | 0 | 0 | 0.01 | 0 | 0 | 0 |
| (9) HPT-7G | 0 | 0 | 0 | 0 | 0 | 0 | 0.01 | 0 | 0 |
| (16) NGN-7G Inclusion Compound-Containing Composition | 0 | 0 | 0 | 0 | 0 | 0 | 0 | 0.01 | 0 |
| (11) NGN-7G | 0 | 0 | 0 | 0 | 0 | 0 | 0 | 0 | 0.01 |
| Stevia extract, % by mass | 0.03 | 0.03 | 0.03 | 0.03 | 0.03 | 0.03 | 0.03 | 0.03 | 0.03 |
| L-Ascorbic acid, % by mass | 0.03 | 0.03 | 0.03 | 0.03 | 0.03 | 0.03 | 0.03 | 0.03 | 0.03 |
| Xylitol, % by mass | 6 | 6 | 6 | 6 | 6 | 6 | 6 | 6 | 6 |
| Black tea flavor, % by mass | 0.1 | 0.1 | 0.1 | 0.1 | 0.1 | 0.1 | 0.1 | 0.1 | 0.1 |
| Distilled water, % by mass | balance | balance | balance | balance | balance | balance | balance | balance | balance |
| Total amount, % by mass | 100 | 100 | 100 | 100 | 100 | 100 | 100 | 100 | 100 |
| Evaluation of Bitterness | 2.8 | 1.3 | 1.0 | 2.7 | 1.4 | 1.3 | 1.0 | 2.8 | 1.0 |

*In the table, (4), (5), and (14) are each an amount 0.01% by mass in terms of a content of isoquercitrin or a conversion value; (7) to (9) and (15) are each an amount 0.01% by mass in terms of a content of hesperetin-7-glucoside or a conversion value; and (11) and (16) are each an amount 0.01% by mass in terms of a content of naringenin-7-glucoside or a conversion value.

5. Coffee Beverages: Improvements in Bitterness

Examples 41 to 43, Comparative Examples 101 to 106

Raw materials as listed in Table 6 were stir-blended, and the mixture was then subjected to a total volume compensation. The mixture was then homogenized with a homogenizer when the temperature reached at 70° C. Thereafter, a 200 mL canister was subjected to retort-sterilization at 121° C. for 15 minutes, to prepare a coffee beverage. The evaluations of bitterness were made in the same manner as in the black tea beverages. The results are shown in Table 6.

The details of the components as listed in Table 6 are the same as Tables 1 to 5, except for those shown hereinbelow.
Coffee extract: (manufactured by GS FOOD CO., LTD.)
Cow's milk: (manufactured by Meiji Dairies Co., Ltd.)
Skim milk powder: (manufactured by Yotsuba Milk Products Co., Ltd.)
Sugar: (manufactured by Mitsui Sugar Co., Ltd.)
Emulsifier: (manufactured by Taiyo Kagaku Co., Ltd.)
Sodium hydrogencarbonate: (manufactured by Taiyo Pharmaceutical Co., LTD.)
Coffee flavor: (OGAWA Flavors & Flagrances Co., Ltd.)
Sucralose: (manufactured by TATE & LYLE)
Erythritol: (manufactured by B Food Science Co., Ltd.)

TABLE 6

| | Ex. 41 | Comp. Ex. 101 | Comp. Ex. 102 | Ex. 42 | Comp. Ex. 103 | Comp. Ex. 104 | Comp. Ex. 105 | Ex. 43 | Comp. Ex. 106 |
|---|---|---|---|---|---|---|---|---|---|
| Coffee extract, % by mass | 32.6 | 32.6 | 32.6 | 32.6 | 32.6 | 32.6 | 32.6 | 32.6 | 32.6 |
| Cow's milk, % by mass | 21 | 21 | 21 | 21 | 21 | 21 | 21 | 21 | 21 |
| Skim milk powder, % by mass | 0.1 | 0.1 | 0.1 | 0.1 | 0.1 | 0.1 | 0.1 | 0.1 | 0.1 |
| Whole milk powder, % by mass | 0.1 | 0.1 | 0.1 | 0.1 | 0.1 | 0.1 | 0.1 | 0.1 | 0.1 |
| Sugar, % by mass | 6 | 6 | 6 | 6 | 6 | 6 | 6 | 6 | 6 |
| Emulsifier, % by mass | 0.18 | 0.18 | 0.18 | 0.18 | 0.18 | 0.18 | 0.18 | 0.18 | 0.18 |
| Sodium hydrogencarbonate, % by mass | 0.12 | 0.12 | 0.12 | 0.12 | 0.12 | 0.12 | 0.12 | 0.12 | 0.12 |
| (14) IQC Inclusion Compound-Containing Composition | 0.03 | 0 | 0 | 0 | 0 | 0 | 0 | 0 | 0 |
| (4) Enzymatically Treated IQC | 0 | 0.03 | 0 | 0 | 0 | 0 | 0 | 0 | 0 |
| (5) IQC | 0 | 0 | 0.03 | 0 | 0 | 0 | 0 | 0 | 0 |
| (15) HPT-7G Inclusion Compound-Containing Composition | 0 | 0 | 0 | 0.03 | 0 | 0 | 0 | 0 | 0 |
| (7) Enzymatically Treated HSP | 0 | 0 | 0 | 0 | 0.03 | 0 | 0 | 0 | 0 |
| (8) Dispersed HPT | 0 | 0 | 0 | 0 | 0 | 0.03 | 0 | 0 | 0 |
| (9) HPT-7G | 0 | 0 | 0 | 0 | 0 | 0 | 0.03 | 0 | 0 |
| (16) NGN-7G Inclusion Compound-Containing Composition | 0 | 0 | 0 | 0 | 0 | 0 | 0 | 0.03 | 0 |
| (11) NGN-7G | 0 | 0 | 0 | 0 | 0 | 0 | 0 | 0 | 0.03 |
| Coffee flavor, % by mass | 0.06 | 0.06 | 0.06 | 0.06 | 0.06 | 0.06 | 0.06 | 0.06 | 0.06 |
| Sucralose, % by mass | 0.014 | 0.014 | 0.014 | 0.014 | 0.014 | 0.014 | 0.014 | 0.014 | 0.014 |
| Erythritol, % by mass | 3 | 3 | 3 | 3 | 3 | 3 | 3 | 3 | 3 |
| Distilled water, % by mass | balance | balance | balance | balance | balance | balance | balance | balance | balance |
| Total amount, % by mass | 100 | 100 | 100 | 100 | 100 | 100 | 100 | 100 | 100 |
| Evaluation of Bitterness | 2.6 | 1.6 | 1.0 | 2.7 | 1.3 | 1.5 | 1.0 | 2.9 | 1.0 |

*In the table, (4), (5), and (14) are each an amount 0.03% by mass in terms of a content of isoquercitrin or a conversion value; (7) to (9) and (15) are each an amount 0.03% by mass in terms of a content of hesperetin-7-glucoside or a conversion value; and (11) and (16) are each an amount 0.03% by mass in terms of a content of naringenin-7-glucoside or a conversion value.

6. Tablets: Improvements in Bitterness

Examples 51 to 53, and Comparative Examples 111 to 116

Raw materials as listed in Table 7 were powder-blended, and tableted with a tableting machine (300 mg per tablet), to prepare a tablet. The bitterness was evaluated in the same manner as in the black tea beverages. The results are shown in Table 7.

The details of the components as listed in Table 7 are the same as Tables 1 to 6, except for those shown hereinbelow.
Sucrose fatty acid ester: (manufactured by Taiyo Kagaku Co., Ltd.)
Citric acid: (manufactured by Taiyo Pharmaceutical Co., LTD.)
Powder pigment: (manufactured by YAEGAKI Bio-Industry, Inc.)
Aspartame (manufactured by AJINOMOTO CO., INC., PAL SWEET)
Acesulfame K (manufactured by Nutrinova, Sunnette)
Crystalline cellulose: (manufactured by Asahi Kasei Corporation)

TABLE 7

|  | Ex. 51 | Comp. Ex. 111 | Comp. Ex. 112 | Ex. 52 | Comp. Ex. 113 | Comp. Ex. 114 | Comp. Ex. 115 | Ex. 53 | Comp. Ex. 116 |
|---|---|---|---|---|---|---|---|---|---|
| Sucrose fatty acid ester, % by mass | 2 | 2 | 2 | 2 | 2 | 2 | 2 | 2 | 2 |
| Citric acid, % by mass | 2 | 2 | 2 | 2 | 2 | 2 | 2 | 2 | 2 |
| Powder pigment, % by mass | 0.4 | 0.4 | 0.4 | 0.4 | 0.4 | 0.4 | 0.4 | 0.4 | 0.4 |
| (14) IQC Inclusion Compound-Containing Composition | 10 | 0 | 0 | 0 | 0 | 0 | 0 | 0 | 0 |
| (4) Enzymatically Treated IQC | 0 | 10 | 0 | 0 | 0 | 0 | 0 | 0 | 0 |
| (5) IQC | 0 | 0 | 10 | 0 | 0 | 0 | 0 | 0 | 0 |
| (15) HPT-7G Inclusion Compound-Containing Composition | 0 | 0 | 0 | 10 | 0 | 0 | 0 | 0 | 0 |
| (7) Enzymatically Treated HSP | 0 | 0 | 0 | 0 | 10 | 0 | 0 | 0 | 0 |
| (8) Dispersed HPT | 0 | 0 | 0 | 0 | 0 | 10 | 0 | 0 | 0 |
| (9) HPT-7G | 0 | 0 | 0 | 0 | 0 | 0 | 10 | 0 | 0 |
| (16) NGN-7G Inclusion Compound-Containing Composition | 0 | 0 | 0 | 0 | 0 | 0 | 0 | 10 | 0 |
| (11) NGN-7G | 0 | 0 | 0 | 0 | 0 | 0 | 0 | 0 | 10 |
| Aspartame, % by mass | 0.03 | 0.03 | 0.03 | 0.03 | 0.03 | 0.03 | 0.03 | 0.03 | 0.03 |
| Acesulfame K, % by mass | 0.05 | 0.05 | 0.05 | 0.05 | 0.05 | 0.05 | 0.05 | 0.05 | 0.05 |
| Crystalline cellulose, % by mass | balance | balance | balance | balance | balance | balance | balance | balance | balance |
| Total amount, % by mass | 100 | 100 | 100 | 100 | 100 | 100 | 100 | 100 | 100 |
| Evaluation of Bitterness | 2.6 | 1.4 | 1.0 | 2.7 | 1.6 | 1.4 | 1.0 | 2.9 | 1.0 |

*In the table, (4), (5), and (14) are each an amount 10% by mass in terms of a content of isoquercitrin or a conversion value; (7) to (9) and (15) are each an amount 10% by mass in terms of a content of hesperetin-7-glucoside or a conversion value; and (11) and (16) are each an amount 10% by mass in terms of a content of naringenin-7-glucoside or a conversion value.

7. Granules: Improvements in Bitterness

Examples 61 to 63, and Comparative Examples 121 to 126

Dextrose monohydrate, sucralose, and a flavonoid listed in Table 8 were powder-blended, and the remaining raw materials as listed in Table 8 were then mixed therewith, while stir-mixing the components with a mixing agitator. After the mixing, the mixture was dried with a hot-air dryer at 60° C. for 2 hours, to produce granules. The evaluations of the bitterness were made in the same manner as in the black tea beverages. The results are shown in Table 8.

The details of the components as listed in Table 8 are the same as Tables 1 to 7, except for those shown hereinbelow.
Green tea powder: (manufactured by ITO EN, LTD.)
Green tea flavor: (manufactured by OGAWA Flavors & Flagrances Co., Ltd.)
Sucralose: (manufactured by TATE & LYLE)
Dextrose monohydrate: (manufactured by San-ei Sucrochemical Co., Ltd.)

TABLE 8

|  | Ex. 61 | Comp. Ex. 121 | Comp. Ex. 122 | Ex. 62 | Comp. Ex. 123 | Comp. Ex. 124 | Comp. Ex. 125 | Ex. 63 | Comp. Ex. 126 |
|---|---|---|---|---|---|---|---|---|---|
| Green tea powder, % by mass | 3 | 3 | 3 | 3 | 3 | 3 | 3 | 3 | 3 |
| Distilled water, % by mass | 5 | 5 | 5 | 5 | 5 | 5 | 5 | 5 | 5 |
| Green tea flavor, % by mass | 1 | 1 | 1 | 1 | 1 | 1 | 1 | 1 | 1 |

TABLE 8-continued

| | Ex. 61 | Comp. Ex. 121 | Comp. Ex. 122 | Ex. 62 | Comp. Ex. 123 | Comp. Ex. 124 | Comp. Ex. 125 | Ex. 63 | Comp. Ex. 126 |
|---|---|---|---|---|---|---|---|---|---|
| (14) IQC Inclusion Compound-Containing Composition | 2 | 0 | 0 | 0 | 0 | 0 | 0 | 0 | 0 |
| (4) Enzymatically Treated IQC | 0 | 2 | 0 | 0 | 0 | 0 | 0 | 0 | 0 |
| (5) IQC | 0 | 0 | 2 | 0 | 0 | 0 | 0 | 0 | 0 |
| (15) HPT-7G Inclusion Compound-Containing Composition | 0 | 0 | 0 | 2 | 0 | 0 | 0 | 0 | 0 |
| (7) Enzymatically Treated HSP | 0 | 0 | 0 | 0 | 2 | 0 | 0 | 0 | 0 |
| (8) Dispersed HPT | 0 | 0 | 0 | 0 | 0 | 2 | 0 | 0 | 0 |
| (9) HPT-7G | 0 | 0 | 0 | 0 | 0 | 0 | 2 | 0 | 0 |
| (16) NGN-7G Inclusion Compound-Containing Composition | 0 | 0 | 0 | 0 | 0 | 0 | 0 | 2 | 0 |
| (11) NGN-7G | 0 | 0 | 0 | 0 | 0 | 0 | 0 | 0 | 2 |
| Sucralose, % by mass | 0.015 | 0.015 | 0.015 | 0.015 | 0.015 | 0.015 | 0.015 | 0.015 | 0.015 |
| Dextrose monohydrate, % by mass | balance | balance | balance | balance | balance | balance | balance | balance | balance |
| Total amount, % by mass | 100 | 100 | 100 | 100 | 100 | 100 | 100 | 100 | 100 |
| Evaluation of Bitterness | 2.5 | 1.7 | 1.0 | 2.6 | 1.4 | 1.5 | 1.0 | 2.6 | 1.0 |

*In the table, (4), (5), and (14) are each an amount 2% by mass in terms of a content of isoquercitrin or a conversion value; (7) to (9) and (15) are each an amount 2% by mass in terms of a content of hesperetin-7-glucoside or a conversion value; and (11) and (16) are each an amount 2% by mass in terms of a content of naringenin-7-glucoside or a conversion value.

8. Hard Yogurt: Improvements in Bitterness

Examples 71 to 73 and Comparative Examples 131 to 136

Raw materials as listed in Table 9 other than a starter and a yogurt flavor were mixed, and stirred at 90° C. for 10 minutes to dissolve. The solution was sterilized at 90° C. for 10 minutes, a sterilized mixture was then cooled to 40° C., and the remaining raw materials were added and mixed. The mixture was filled in a 100 ml plastic cup, and fermented in a thermostat held at 40° C. to a pH of 4.5, and the mixture was then cooled, to prepare a hard yogurt. The evaluations of the bitterness were made in the same manner as in the black tea beverages. The results are shown in Table 9.

The details of the components listed in Table 9 are the same as those of Tables 1 to 8 except for those shown hereinbelow.

Cow's milk: (manufactured by Meiji Dairies Co., Ltd.)
Skim milk powder: (manufactured by Yotsuba Milk Products Co., Ltd.)
Sugar: (manufactured by Mitsui Sugar Co., Ltd.)
Sorbitol: (manufactured by B Food Science Co., Ltd., Sorbitol SP)
Gelating agent: (Nitta Gelatin, Inc.)
Yogurt flavor: (manufactured by OGAWA Flavors & Flagrances Co., Ltd.)
Starter: (manufactured by FUJICCO Co., Ltd.)

TABLE 9

| | Ex. 71 | Comp. Ex. 131 | Comp. Ex. 132 | Ex. 72 | Comp. Ex. 133 | Comp. Ex. 134 | Comp. Ex. 135 | Ex. 73 | Comp. Ex. 136 |
|---|---|---|---|---|---|---|---|---|---|
| Cow's milk, % by mass | 80 | 80 | 80 | 80 | 80 | 80 | 80 | 80 | 80 |
| Skim milk powder, % by mass | 2 | 2 | 2 | 2 | 2 | 2 | 2 | 2 | 2 |
| Sugar, % by mass | 8 | 8 | 8 | 8 | 8 | 8 | 8 | 8 | 8 |
| Sorbitol, % by mass | 4 | 4 | 4 | 4 | 4 | 4 | 4 | 4 | 4 |
| Gelating agent, % by mass | 0.5 | 0.5 | 0.5 | 0.5 | 0.5 | 0.5 | 0.5 | 0.5 | 0.5 |
| Yogurt flavor, % by mass | 0.1 | 0.1 | 0.1 | 0.1 | 0.1 | 0.1 | 0.1 | 0.1 | 0.1 |
| Starter, % by mass | 3 | 3 | 3 | 3 | 3 | 3 | 3 | 3 | 3 |
| (14) IQC Inclusion Compound-Containing Composition | 0.05 | 0 | 0 | 0 | 0 | 0 | 0 | 0 | 0 |
| (4) Enzymatically Treated IQC | 0 | 0.05 | 0 | 0 | 0 | 0 | 0 | 0 | 0 |
| (5) IQC | 0 | 0 | 0.05 | 0 | 0 | 0 | 0 | 0 | 0 |
| (15) HPT-7G Inclusion Compound-Containing Composition | 0 | 0 | 0 | 0.05 | 0 | 0 | 0 | 0 | 0 |
| (7) Enzymatically Treated HSP | 0 | 0 | 0 | 0 | 0.05 | 0 | 0 | 0 | 0 |
| (8) Dispersed HPT | 0 | 0 | 0 | 0 | 0 | 0.05 | 0 | 0 | 0 |
| (9) HPT-7G | 0 | 0 | 0 | 0 | 0 | 0 | 0.05 | 0 | 0 |
| (16) NGN-7G Inclusion Compound-Containing Composition | 0 | 0 | 0 | 0 | 0 | 0 | 0 | 0.05 | 0 |
| (11) NGN-7G | 0 | 0 | 0 | 0 | 0 | 0 | 0 | 0 | 0.05 |
| Distilled water, % by mass | balance | balance | balance | balance | balance | balance | balance | balance | balance |
| Total amount, % by mass | 100 | 100 | 100 | 100 | 100 | 100 | 100 | 100 | 100 |
| Evaluation of Bitterness | 2.8 | 1.3 | 1.0 | 2.5 | 1.2 | 1.8 | 1.0 | 2.4 | 1.0 |

*In the table, (4), (5), and (14) are each an amount 0.05% by mass in terms of a content of isoquercitrin or a conversion value; (7) to (9) and (15) are each an amount 0.05% by mass in terms of a content of hesperetin-7-glucoside or a conversion value; and (11) and (16) are each an amount 0.05% by mass in terms of a content of naringenin-7-glucoside or a conversion value.

As shown in Examples 31 to 73 of Tables 5 to 9, it could be seen that the bitterness significantly improved even when a composition containing a flavonoid inclusion compound and a rhamnose is added as an embodiment of adding a flavonoid inclusion compound. Here, although not indicated in the tables, the sensory evaluations were made on a flavonoid (isoquercitrin, hesperetin-7-glucoside, or naringenin-7-glucoside) inclusion compound from which a rhamnose was removed, and as a result, the evaluations had lower scores by 0.1 to 0.2.

9. Acidic Solutions and Commercially Available Solutions: Improvements in Unpleasant Taste Examples 81 to 168, Comparative Examples 141 to 318, and Reference Examples 21 to 48

Isoquercitrin, hesperetin-7-glucoside, or naringenin-7-glucoside was added in an amount of which content or a conversion amount was 0.003% by mass to each of test solutions containing materials as listed in Tables 10 to 13 (pH 3, 0.08% by mass of citric acid, the pH being adjusted with trisodium citrate), and commercially available beverages listed in Tables 14 to 17.

The details of the components listed in Tables 10 to 17 are the same as those of Tables 1 to 9 except for those shown hereinbelow.

(23) IQC+γCD: Separately adding and mixing 0.003% by mass of isoquercitrin of Preparation Example 1 and 0.009% by mass of γ-cyclodextrin (manufactured by PEARL ACE CORPORATION) to a beverage Acesulfame K (manufactured by Maruzen Chemicals Co., Ltd.)
Tannin: (FUJI CHEMICAL INDUSTRY CO., LTD.)
Caffeine: (manufactured by nacalai tesque)
Chlorogenic acid: (manufactured by nacalai tesque)
Catechin: (manufactured by Taiyo Kagaku Co., Ltd.)
Tea extract: (manufactured by MITSUBISHI-CHEMICAL FOODS CORPORATION)
Commercially Available Beverage A: Coca-Cola Zero (manufactured by Coca-Cola (Japan) Company, Limited), (containing sucralose, acesulfame K)
Commercially Available Beverage B: Healthya Coffee, Sugar-Free, Black (manufactured by Kao Corporation), (containing chlorogenic acid, caffeine)
Commercially Available Beverage C: WONDA KIWAMI BLACK, Kanjuku Fukairi (supreme, black, fully matured, deeply roasted) (manufactured by Asahi Soft Drinks Co., Ltd.), (containing caffeine)
Commercially Available Beverage D: C. C. Lemon (manufactured by SUNTORY BEVERAGE & FOOD LIMITED), (containing vitamin C)
Commercially Available Beverage E: Gogo-no-Kocha (Japanese Afternoon Black Tea) Oishii Sugar-Free (Tasty, Sugar-Free) (manufactured by Kirin Beverage Company, Limited), (containing tannin)
Commercially Available Beverage F: Dekavita C 0(Zero) (manufactured by SUNTORY FOODS LIMITED, (containing erythritol)
Commercially Available Beverage G: Chuhai Taste Lemon (manufactured by Japan Sangaria Beverage Company, Limited), (containing erythritol)
Commercially Available Beverage H: Healthya Green Tea (manufactured by Kao Corporation), (containing catechin)

<Effects of Improving Unpleasant Taste>

As to the sensory evaluations regarding unpleasant tastes of Examples 81 to 168, Comparative Examples 141 to 318, and Reference Examples 21 to 48, the effects of improvements in lingering sweet taste, sweetness, acridity, acerbity, or acidic taste were evaluated by 10 panelists for every material solutions and every beverages, and the components of the same kinds were compared (among (1), (2), (23), (4), and (5), among (6), (8), and (9), and among (10) and (11)), and the number of persons that evaluated on the improvements in the unpleasant taste was recorded. The results are shown in Tables 10 to 17. Here, "lingering sweet taste" listed as an unpleasant taste refers to worsening of cut-off of a lingering taste due to persistent sweet taste. Also, the "sweetness" listed as an unpleasant taste refers to a disagreeable taste due to a sweetener other than sugars. Therefore, those with improvement in cut-off of a lingering taste were evaluated as improvement in "lingering sweet taste," and those nearing the sweetener of sugars were evaluated as improvement in "sweetness."

TABLE 10

| Test Solution, pH 3.1 | Unpleasant Taste | (1) IQC-γCD Inclusion Compound (Enzyme Method) | | (2) IQC-γCD Inclusion Compound (Dissolution Method) | |
|---|---|---|---|---|---|
| Sucralose, 0.04% by mass | Lingering sweet taste | Ex. 81 | 5 | Ref. Ex. 21 | 3 |
| Aspartame, 0.1% by mass | Lingering sweet taste | Ex. 82 | 7 | Ref. Ex. 22 | 2 |
| Acesulfame K, 0.15% by mass | Lingering sweet taste | Ex. 83 | 6 | Ref. Ex. 23 | 3 |
| Stevia extract, 0.15% by mass | Lingering sweet taste | Ex. 84 | 6 | Ref. Ex. 24 | 2 |
| Erythritol, 24% by mass | Sweetness | Ex. 85 | 5 | Ref. Ex. 25 | 4 |
| Sorbitol, 27% by mass | Sweetness | Ex. 86 | 7 | Ref. Ex. 26 | 2 |
| Xylitol, 18% by mass | Sweetness | Ex. 87 | 6 | Ref. Ex. 27 | 2 |
| Catechin, 0.2 | Bitterness | Ex. 88 | 6 | Ref. Ex. 28 | 3 |
| Tea extract, 0.1 | Acerbity | Ex. 89 | 6 | Ref. Ex. 29 | 1 |
| Chlorogenic acid, 0.05 | Acridity | Ex. 90 | 7 | Ref. Ex. 30 | 1 |
| Tannin, 0.05 | Acerbity | Ex. 91 | 5 | Ref. Ex. 31 | 3 |

TABLE 10-continued

| Test Solution, pH 3.1 | Unpleasant Taste | | | (1) IQC-γCD Inclusion Compound (Enzyme Method) | | (2) IQC-γCD Inclusion Compound (Dissolution Method) |
|---|---|---|---|---|---|---|
| Caffeine, 0.2 | Bitterness | Ex. 92 | 6 | Ref. Ex. 32 | | 3 |
| Ascorbic acid, 0.3 | Acidic Taste | Ex. 93 | 8 | Ref. Ex. 33 | | 1 |

*In the table, (1) and (2) are each an amount 0.003% by mass in terms of a content of isoquercitrin or a conversion value.

TABLE 11

| Test Solution, pH 3.1 | Unpleasant Taste | (23) IQC + γCD | | (4) Enzymatically Treated IQC | | (5) IQC | |
|---|---|---|---|---|---|---|---|
| Sucralose, 0.04% by mass | Lingering sweet taste | Comp. Ex. 141 | 1 | Comp. Ex. 161 | 1 | Comp. Ex. 181 | 0 |
| Aspartame, 0.1% by mass | Lingering sweet taste | Comp. Ex. 142 | 1 | Comp. Ex. 162 | 0 | Comp. Ex. 182 | 0 |
| Acesulfame K, 0.15% by mass | Lingering sweet taste | Comp. Ex. 143 | 0 | Comp. Ex. 163 | 1 | Comp. Ex. 183 | 0 |
| Stevia extract, 0.15% by mass | Lingering sweet taste | Comp. Ex. 144 | 1 | Comp. Ex. 164 | 0 | Comp. Ex. 184 | 1 |
| Erythritol, 24% by mass | Sweetness | Comp. Ex. 145 | 1 | Comp. Ex. 165 | 0 | Comp. Ex. 185 | 0 |
| Sorbitol, 27% by mass | Sweetness | Comp. Ex. 146 | 1 | Comp. Ex. 166 | 0 | Comp. Ex. 186 | 0 |
| Xylitol, 18% by mass | Sweetness | Comp. Ex. 147 | 1 | Comp. Ex. 167 | 0 | Comp. Ex. 187 | 1 |
| Catechin, 0.2 | Bitterness | Comp. Ex. 148 | 1 | Comp. Ex. 168 | 0 | Comp. Ex. 188 | 0 |
| Tea extract, 0.1 | Acerbity | Comp. Ex. 149 | 1 | Comp. Ex. 169 | 1 | Comp. Ex. 189 | 1 |
| Chlorogenic acid, 0.05 | Acridity | Comp. Ex. 150 | 1 | Comp. Ex. 170 | 0 | Comp. Ex. 190 | 1 |
| Tannin, 0.05 | Acerbity | Comp. Ex. 151 | 1 | Comp. Ex. 171 | 0 | Comp. Ex. 191 | 1 |
| Caffeine, 0.2 | Bitterness | Comp. Ex. 152 | 1 | Comp. Ex. 172 | 0 | Comp. Ex. 192 | 0 |
| Ascorbic acid, 0.3 | Acidic Taste | Comp. Ex. 153 | 1 | Comp. Ex. 173 | 0 | Comp. Ex. 193 | 0 |

*In the table, (23), (4) and (5) are each an amount 0.003% by mass in terms of a content of isoquercitrin or a conversion value.

TABLE 12

| Test Solution, pH 3.1 | Unpleasant Taste | (6) HPT-7G-βCD Inclusion Compound (Enzyme Method) | | (8) Dispersed HPT | | (9) HPT-7G | |
|---|---|---|---|---|---|---|---|
| Sucralose, 0.04% by mass | Lingering sweet taste | Ex. 101 | 7 | Comp. Ex. 201 | 1 | Comp. Ex. 221 | 2 |
| Aspartame, 0.1% by mass | Lingering sweet taste | Ex. 102 | 8 | Comp. Ex. 202 | 1 | Comp. Ex. 222 | 1 |
| Acesulfame K, 0.15% by mass | Lingering sweet taste | Ex. 103 | 6 | Comp. Ex. 203 | 3 | Comp. Ex. 223 | 1 |
| Stevia extract, 0.15% by mass | Lingering sweet taste | Ex. 104 | 7 | Comp. Ex. 204 | 2 | Comp. Ex. 224 | 1 |
| Erythritol, 24% by mass | Sweetness | Ex. 105 | 6 | Comp. Ex. 205 | 2 | Comp. Ex. 225 | 2 |
| Sorbitol, 27% by mass | Sweetness | Ex. 106 | 7 | Comp. Ex. 206 | 2 | Comp. Ex. 226 | 1 |
| Xylitol, 18% by mass | Sweetness | Ex. 107 | 8 | Comp. Ex. 207 | 2 | Comp. Ex. 227 | 0 |
| Catechin, 0.2 | Bitterness | Ex. 108 | 8 | Comp. Ex. 208 | 2 | Comp. Ex. 228 | 0 |
| Tea extract, 0.1 | Acerbity | Ex. 109 | 7 | Comp. Ex. 209 | 2 | Comp. Ex. 229 | 1 |
| Chlorogenic acid, 0.05 | Acridity | Ex. 110 | 8 | Comp. Ex. 210 | 1 | Comp. Ex. 230 | 1 |
| Tannin, 0.05 | Acerbity | Ex. 111 | 7 | Comp. Ex. 211 | 1 | Comp. Ex. 231 | 2 |

TABLE 12-continued

| Test Solution, pH 3.1 | Unpleasant Taste | (6) HPT-7G-βCD Inclusion Compound (Enzyme Method) | | (8) Dispersed HPT | | (9) HPT-7G | |
|---|---|---|---|---|---|---|---|
| Caffeine, 0.2 | Bitterness | Ex. 112 | 8 | Comp. Ex. 212 | 1 | Comp. Ex. 232 | 1 |
| Ascorbic acid, 0.3 | Acidic Taste | Ex. 113 | 6 | Comp. Ex. 213 | 2 | Comp. Ex. 233 | 2 |

*In the table, (6), (8), and (9) are each an amount 0.003% by mass in terms of a content of hesperetin-7-glucoside or a conversion value.

TABLE 13

| Test Solution, pH 3.1 | Unpleasant Taste | (10) NGN-7G-βCD Inclusion Compound (Enzyme Method) | | (11) NGN-7G | |
|---|---|---|---|---|---|
| Sucralose, 0.04% by mass | Lingering sweet taste | Ex. 121 | 8 | Comp. Ex. 241 | 2 |
| Aspartame, 0.1% by mass | Lingering sweet taste | Ex. 122 | 7 | Comp. Ex. 242 | 3 |
| Acesulfame K, 0.15% by mass | Lingering sweet taste | Ex. 123 | 8 | Comp. Ex. 243 | 2 |
| Stevia extract, 0.15% by mass | Lingering sweet taste | Ex. 124 | 8 | Comp. Ex. 244 | 2 |
| Erythritol, 24% by mass | Sweetness | Ex. 125 | 7 | Comp. Ex. 245 | 3 |
| Sorbitol, 27% by mass | Sweetness | Ex. 126 | 8 | Comp. Ex. 246 | 2 |
| Xylitol, 18% by mass | Sweetness | Ex. 127 | 9 | Comp. Ex. 247 | 1 |
| Catechin, 0.2 | Bitterness | Ex. 128 | 8 | Comp. Ex. 248 | 2 |
| Tea extract, 0.1 | Acerbity | Ex. 129 | 9 | Comp. Ex. 249 | 1 |
| Chlorogenic acid, 0.05 | Acridity | Ex. 130 | 7 | Comp. Ex. 250 | 3 |
| Tannin, 0.05 | Acerbity | Ex. 131 | 6 | Comp. Ex. 251 | 4 |
| Caffeine, 0.2 | Bitterness | Ex. 132 | 7 | Comp. Ex. 252 | 3 |
| Ascorbic acid, 0.3 | Acidic Taste | Ex. 133 | 7 | Comp. Ex. 253 | 3 |

*In the table, (10) and (11) are each an amount 0.003% by mass in terms of a content of naringenin-7-glucoside or a conversion value.

TABLE 14

| Commercially Available Beverage | Unpleasant Taste | (1) IQC-γCD Inclusion Compound (Enzyme Method) | | (2) IQC-γCD Inclusion Compound (Dissolution Method) | |
|---|---|---|---|---|---|
| Commercially Available Beverage A | Lingering sweet taste | Ex. 141 | 6 | Ref. Ex. 41 | 2 |
| Commercially Available Beverage B | Bitterness | Ex. 142 | 5 | Ref. Ex. 42 | 2 |
| Commercially Available Beverage C | Acridity | Ex. 143 | 6 | Ref. Ex. 43 | 2 |
| Commercially Available Beverage D | Acidic Taste | Ex. 144 | 8 | Ref. Ex. 44 | 2 |
| Commercially Available Beverage E | Acridity | Ex. 145 | 6 | Ref. Ex. 45 | 3 |
| Commercially Available Beverage F | Sweetness | Ex. 146 | 5 | Ref. Ex. 46 | 2 |
| Commercially Available Beverage G | Sweetness | Ex. 147 | 6 | Ref. Ex. 47 | 3 |
| Commercially Available Beverage H | Bitterness | Ex. 148 | 7 | Ref. Ex. 48 | 1 |

*In the table, (1) and (2) are each an amount 0.003% by mass in terms of a content of isoquercitrin or a conversion value

TABLE 15

| Commercially Available Beverage | Unpleasant Taste | (23) IQC + γCD | | (4) Enzymatically Treated IQC | | (5) IQC | |
|---|---|---|---|---|---|---|---|
| Commercially Available Beverage A | Lingering sweet taste | Comp. Ex. 261 | 1 | Comp. Ex. 271 | 0 | Comp. Ex. 281 | 1 |
| Commercially Available Beverage B | Bitterness | Comp. Ex. 262 | 1 | Comp. Ex. 272 | 1 | Comp. Ex. 282 | 1 |
| Commercially Available Beverage C | Acridity | Comp. Ex. 263 | 1 | Comp. Ex. 273 | 0 | Comp. Ex. 283 | 1 |
| Commercially Available Beverage D | Acidic Taste | Comp. Ex. 264 | 0 | Comp. Ex. 274 | 0 | Comp. Ex. 284 | 0 |
| Commercially Available Beverage E | Acridity | Comp. Ex. 265 | 1 | Comp. Ex. 275 | 0 | Comp. Ex. 285 | 0 |
| Commercially Available Beverage F | Sweetness | Comp. Ex. 266 | 1 | Comp. Ex. 276 | 1 | Comp. Ex. 286 | 1 |
| Commercially Available Beverage G | Sweetness | Comp. Ex. 267 | 0 | Comp. Ex. 277 | 0 | Comp. Ex. 287 | 1 |
| Commercially Available Beverage H | Bitterness | Comp. Ex. 268 | 1 | Comp. Ex. 278 | 0 | Comp. Ex. 288 | 1 |

*In the table, (23), (4) and (5) are each an amount 0.003% by mass in terms of a content of isoquercitrin or a conversion value.

TABLE 16

| Commercially Available Beverage | Unpleasant Taste | (6) HPT-7G-βCD Inclusion Compound (Enzyme Method) | | (8) Dispersed HPT | | (9) HPT-7G | |
|---|---|---|---|---|---|---|---|
| Commercially Available Beverage A | Lingering sweet taste | Ex. 151 | 7 | Comp. Ex. 291 | 1 | Comp. Ex. 301 | 2 |
| Commercially Available Beverage B | Bitterness | Ex. 152 | 8 | Comp. Ex. 292 | 1 | Comp. Ex. 302 | 1 |
| Commercially Available Beverage C | Acridity | Ex. 153 | 7 | Comp. Ex. 293 | 1 | Comp. Ex. 303 | 2 |
| Commercially Available Beverage D | Acidic Taste | Ex. 154 | 8 | Comp. Ex. 294 | 1 | Comp. Ex. 304 | 1 |
| Commercially Available Beverage E | Acridity | Ex. 155 | 8 | Comp. Ex. 295 | 1 | Comp. Ex. 305 | 1 |
| Commercially Available Beverage F | Sweetness | Ex. 156 | 7 | Comp. Ex. 296 | 1 | Comp. Ex. 306 | 2 |
| Commercially Available Beverage G | Sweetness | Ex. 157 | 7 | Comp. Ex. 297 | 1 | Comp. Ex. 307 | 2 |
| Commercially Available Beverage H | Bitterness | Ex. 158 | 8 | Comp. Ex. 298 | 1 | Comp. Ex. 308 | 1 |

*In the table, (6), (8), and (9) are each an amount 0.003% by mass in terms of a content of hesperetin-7-glucoside or a conversion value.

TABLE 17

| Commercially Available Beverage | Unpleasant Taste | (10) NGN-7G-βCD Inclusion Compound (Enzyme Method) | | (11) NGN-7G | |
|---|---|---|---|---|---|
| Commercially Available Beverage A | Lingering sweet taste | Ex. 161 | 8 | Comp. Ex. 311 | 2 |
| Commercially Available Beverage B | Bitterness | Ex. 162 | 7 | Comp. Ex. 312 | 3 |
| Commercially Available Beverage C | Acridity | Ex. 163 | 6 | Comp. Ex. 313 | 4 |
| Commercially Available Beverage D | Acidic Taste | Ex. 164 | 7 | Comp. Ex. 314 | 3 |
| Commercially Available Beverage E | Acridity | Ex. 165 | 8 | Comp. Ex. 315 | 2 |
| Commercially Available Beverage F | Sweetness | Ex. 166 | 8 | Comp. Ex. 316 | 2 |
| Commercially Available Beverage G | Sweetness | Ex. 167 | 9 | Comp. Ex. 317 | 1 |
| Commercially Available Beverage H | Bitterness | Ex. 168 | 8 | Comp. Ex. 318 | 2 |

*In the table, (10) and (11) are each an amount 0.003% by mass in terms of a content of naringenin-7-glucoside or a conversion value.

As shown in Tables 10 to 17, the most improvement in unpleasant taste of the test solutions and the commercially available beverages was shown in (1) the isoquercitrin-cyclodextrin inclusion compound (enzyme method) in the comparisons of the beverages containing isoquercitrin, and in (6) the hesperetin-7-glucoside inclusion compound (enzyme method) in the comparisons of the beverages containing hesperetin, and in (10) the naringenin-7-glucoside inclusion compound (enzyme method) in the comparisons of the beverages containing naringenin. In addition, the same results were obtained even when the compositions obtained in Preparation Examples 8 to 10 were used in place of the flavonoid inclusion compounds obtained by the enzyme method of the above (1), (6), and (10).

10. Acidic Beverages and Tablets: Improvements in Lingering Metallic Taste and Lingering Acidic Taste of Flavonoids Examples 171 to 194, Comparative Examples 321 to 376, and Reference Examples 51 to 58

An acidic beverage containing an isoquercitrin-γ-cyclodextrin inclusion compound of Preparation Example 4 in an amount of 0.007% by mass in terms of an isoquercitrin content and a rhamnose in an amount such that a molar ratio of the rhamnose to the isoquercitrin (rhamnose/isoquercitrin) was as listed in any one of Tables 18 to 21 (pH 3, 0.08% by mass of citric acid, the pH being adjusted with trisodium citrate).

Examples 201 to 224, Comparative Examples 381 to 436, and Reference Examples 61 to 68

A mixture of an isoquercitrin-γ-cyclodextrin inclusion compound of Preparation Example 4 in an amount of 2% by mass in terms of the content of isoquercitrin, a rhamnose in an amount such that a molar ratio of the rhamnose to the isoquercitrin (rhamnose/isoquercitrin) was as listed in any one of Tables 22 to 25, 0.5% by mass of fine silicon dioxide particles, 2.5% by mass of citric acid, and balance a crystalline cellulose was each pressure-molded at a pressure of 100 kg/cm$^2$ in the same manner as in Example 21, to produce a tablet having a diameter of 9 mm and a weight of 300 mg.

The details of the components listed in Tables 18 to 25 are the same as those of Tables 1 to 9.

<Evaluations of Lingering Metallic Taste and Lingering Acidic Taste>

As to the sensory evaluations on the lingering metallic taste and/or lingering acidic taste (tastes that are completely different from bitterness, acerbity, and bitter-and-acerb taste) of Examples 171 to 224, Comparative Examples 321 to 436, and Reference Examples 51 to 68, the evaluations were made in the same manner as in the lemon beverages by comparing among the acidic beverages or among the tablets each containing the components of the same kinds. Specifically, in the comparisons of the components of the same kinds, the one with the strongest lingering metallic taste and/or lingering acidic taste of a flavonoid was given an evaluation score of 1, and each was relatively evaluated thereto. One added in an amount of 0.0007% by mass (1/10 amount of the amount of the flavonoid alone added to the beverage) in the acidic beverage, or one added in an amount of 0.2% by mass (1/10 amount of the amount of the flavonoid alone added to the tablet) was evaluated with a score 5. The evaluations were made by five panelists, and a mean score of total points was calculated. The results are shown in Tables 18 to 25. Here, the tablets were subjected to sensory evaluation for lingering metallic taste and/or lingering acidic taste when two tablets were chewed up and swallowed, the mouth was then washed up with 50 ml of water several times, and the taste lingering after swallowing saliva was evaluated.

(Evaluation Criteria)

1: The lingering metallic taste and/or lingering acidic taste is the strongest, with a very poor balance in the components of the same kinds.

2: The lingering metallic taste and/or lingering acidic taste is somewhat stronger, with a poor balance.

3: The lingering metallic taste and/or lingering acidic taste is somewhat weaker.

4: The lingering metallic taste and/or lingering acidic taste is weaker.

5: The lingering metallic taste and/or lingering acidic taste is very weak, with a very good balance.

TABLE 18

| | Evaluations of Lingering Metallic Taste and Lingering Acidic Taste | | | | | |
|---|---|---|---|---|---|---|
| | Rhamnose Without Addition | | Rhamnose/Flavonoid, molar ratio: 0.1 | | Rhamnose/Flavonoid, molar ratio: 0.8 | |
| (1) IQC-γCD Inclusion Compound (Enzyme Method) | Ex. 171 | 2.4 | Ex. 174 | 3.0 | Ex. 177 | 4.2 |
| (2) IQC-γCD Inclusion Compound (Dissolution Method) | Ref. Ex. 51 | 1.5 | Ref. Ex. 52 | 1.8 | Ref. Ex. 53 | 2.1 |
| (3) IQC + γCD | Comp. Ex. 321 | 1.1 | Comp. Ex. 328 | 1.4 | Comp. Ex. 335 | 1.5 |
| (4) Enzymatically Treated IQC | Comp. Ex. 322 | 1.4 | Comp. Ex. 329 | 1.5 | Comp. Ex. 336 | 1.6 |
| (5) IQC | Comp. Ex. 323 | 1.0 | Comp. Ex. 330 | 1.3 | Comp. Ex. 337 | 1.4 |
| (6) HPT-7G-βCD Inclusion Compound (Enzyme Method) | Ex. 172 | 2.0 | Ex. 175 | 2.9 | Ex. 178 | 4.1 |
| (7) Enzymatically Treated HSP | Comp. Ex. 324 | 1.4 | Comp. Ex. 331 | 1.5 | Comp. Ex. 338 | 2.0 |
| (8) Dispersed HPT | Comp. Ex. 325 | 1.4 | Comp. Ex. 332 | 1.7 | Comp. Ex. 339 | 2.1 |
| (9) HPT-7G | Comp. Ex. 326 | 1.0 | Comp. Ex. 333 | 1.2 | Comp. Ex. 340 | 1.3 |

TABLE 18-continued

|  | Evaluations of Lingering Metallic Taste and Lingering Acidic Taste | | | | | |
|---|---|---|---|---|---|---|
|  | Rhamnose Without Addition | | Rhamnose/ Flavonoid, molar ratio: 0.1 | | Rhamnose/ Flavonoid, molar ratio: 0.8 | |
| (10) NGN-7G-βCD Inclusion Compound (Enzyme Method) | Ex. 173 | 2.3 | Ex. 176 | 2.9 | Ex. 179 | 3.9 |
| (11) NGN-7G | Comp. Ex. 327 | 1.0 | Comp. Ex. 334 | 1.2 | Comp. Ex. 341 | 1.3 |

*In the table, (1) to (5) are each an amount 0.007% by mass in terms of a content of isoquercitrin or a conversion value; (6) to (9) are each an amount 0.007% by mass in terms of a content of hesperetin-7-glucoside or a conversion value; and (10) and (11) are each an amount 0.007% by mass in terms of a content of naringenin-7-glucoside or a conversion value.

TABLE 19

|  | Evaluations of Lingering Metallic Taste and Lingering Acidic Taste | | | |
|---|---|---|---|---|
|  | Rhamnose/ Flavonoid, molar ratio: 1.0 | | Rhamnose/ Flavonoid, molar ratio: 1.2 | |
| (1) IQC-γCD Inclusion Compound (Enzyme Method) | Ex. 180 | 4.7 | Ex. 183 | 4.1 |
| (2) IQC-γCD Inclusion Compound (Dissolution Method) | Ref. Ex. 54 | 2.3 | Ref. Ex. 55 | 2.1 |
| (3) IQC + γCD | Comp. Ex. 342 | 1.6 | Comp. Ex. 349 | 1.5 |
| (4) Enzymatically Treated IQC | Comp. Ex. 343 | 1.7 | Comp. Ex. 350 | 1.5 |
| (5) IQC | Comp. Ex. 344 | 1.5 | Comp. Ex. 351 | 1.4 |
| (6) HPT-7G-βCD Inclusion Compound (Enzyme Method) | Ex. 181 | 4.6 | Ex. 184 | 4.2 |
| (7) Enzymatically Treated HSP | Comp. Ex. 345 | 2.1 | Comp. Ex. 352 | 1.8 |
| (8) Dispersed HPT | Comp. Ex. 346 | 2.5 | Comp. Ex. 353 | 2.2 |
| (9) HPT-7G | Comp. Ex. 347 | 1.4 | Comp. Ex. 354 | 1.3 |
| (10) NGN-7G-βCD Inclusion Compound (Enzyme Method) | Ex. 182 | 4.4 | Ex. 185 | 3.8 |
| (11) NGN-7G | Comp. Ex. 348 | 1.4 | Comp. Ex. 355 | 1.3 |

*In the table, (1) to (5) are each an amount 0.007% by mass in terms of a content of isoquercitrin or a conversion value; (6) to (9) are each an amount 0.007% by mass in terms of a content of hesperetin-7-glucoside or a conversion value; and (10) and (11) are each an amount 0.007% by mass in terms of a content of naringenin-7-glucoside or a conversion value.

TABLE 20

|  | Evaluations of Lingering Metallic Taste and Lingering Acidic Taste | | | |
|---|---|---|---|---|
|  | Rhamnose/ Flavonoid, molar ratio: 2.0 | | Rhamnose/ Flavonoid, molar ratio: 5.0 | |
| (1) IQC-γCD Inclusion Compound (Enzyme Method) | Ex. 186 | 3.9 | Ex. 189 | 3.8 |
| (2) IQC-γCD Inclusion Compound (Dissolution Method) | Ref. Ex. 56 | 2.0 | Ref. Ex. 57 | 2.0 |
| (3) IQC + γCD | Comp. Ex. 356 | 1.4 | Comp. Ex. 363 | 1.3 |
| (4) Enzymatically Treated IQC | Comp. Ex. 357 | 1.4 | Comp. Ex. 364 | 1.3 |
| (5) IQC | Comp. Ex. 358 | 1.3 | Comp. Ex. 365 | 1.2 |
| (6) HPT-7G-βCD Inclusion Compound (Enzyme Method) | Ex. 187 | 4.0 | Ex. 190 | 3.9 |
| (7) Enzymatically Treated HSP | Comp. Ex. 359 | 1.7 | Comp. Ex. 366 | 1.7 |
| (8) Dispersed HPT | Comp. Ex. 360 | 2.2 | Comp. Ex. 367 | 2.1 |
| (9) HPT-7G | Comp. Ex. 361 | 1.2 | Comp. Ex. 368 | 1.2 |
| (10) NGN-7G-βCD Inclusion Compound (Enzyme Method) | Ex. 188 | 3.3 | Ex. 191 | 3.2 |
| (11) NGN-7G | Comp. Ex. 362 | 1.2 | Comp. Ex. 369 | 1.2 |

*In the table, (1) to (5) are each an amount 0.007% by mass in terms of a content of isoquercitrin or a conversion value; (6) to (9) are each an amount 0.007% by mass in terms of a content of hesperetin-7-glucoside or a conversion value; and (10) and (11) are each an amount 0.007% by mass in terms of a content of naringenin-7-glucoside or a conversion value.

TABLE 21

| | | Evaluations of Lingering Metallic Taste and Lingering Acidic Taste |
|---|---|---|
| | | Rhamnose/ Flavonoid, molar ratio: 10.0 |
| (1) IQC-γCD Inclusion Compound (Enzyme Method) | Ex. 192 | 3.7 |
| (2) IQC-γCD Inclusion Compound (Dissolution Method) | Ref. Ex. 58 | 1.9 |
| (3) IQC + γCD | Comp. Ex. 370 | 1.2 |
| (4) Enzymatically Treated IQC | Comp. Ex. 371 | 1.3 |
| (5) IQC | Comp. Ex. 372 | 1.1 |
| (6) HPT-7G-βCD Inclusion Compound (Enzyme Method) | Ex. 193 | 3.8 |
| (7) Enzymatically Treated HSP | Comp. Ex. 373 | 1.6 |
| (8) Dispersed HPT | Comp. Ex. 374 | 2.0 |
| (9) HPT-7G | Comp. Ex. 375 | 1.2 |
| (10) NGN-7G-βCD Inclusion Compound (Enzyme Method) | Ex. 194 | 3.2 |
| (11) NGN-7G | Comp. Ex. 376 | 1.2 |

*In the table, (1) to (5) are each an amount 0.007% by mass in terms of a content of isoquercitrin or a conversion value; (6) to (9) are each an amount 0.007% by mass in terms of a content of hesperetin-7-glucoside or a conversion value; and (10) and (11) are each an amount 0.007% by mass in terns of a content of naringenin-7-glucoside or a conversion value.

TABLE 22

| | Evaluations of Lingering Metallic Taste and Lingering Acidic Taste | | | | | |
|---|---|---|---|---|---|---|
| | Rhamnose Without Addition | | Rhamnose/ Flavonoid, molar ratio: 0.1 | | Rhamnose/ Flavonoid, molar ratio: 0.8 | |
| (1) IQC-γCD Inclusion Compound (Enzyme Method) | Ex. 201 | 2.0 | Ex. 204 | 2.9 | Ex. 207 | 4.1 |
| (2) IQC-γCD Inclusion Compound (Dissolution Method) | Ref. Ex. 61 | 1.4 | Ref. Ex. 62 | 1.7 | Ref. Ex. 63 | 2.2 |
| (3) IQC + γCD | Comp. Ex. 381 | 1.2 | Comp. Ex. 388 | 1.4 | Comp. Ex. 395 | 1.5 |
| (4) Enzymatically Treated IQC | Comp. Ex. 382 | 1.3 | Comp. Ex. 389 | 1.4 | Comp. Ex. 396 | 1.6 |
| (5) IQC | Comp. Ex. 383 | 1.0 | Comp. Ex. 390 | 1.3 | Comp. Ex. 397 | 1.4 |
| (6) HPT-7G-βCD Inclusion Compound (Enzyme Method) | Ex. 202 | 1.9 | Ex. 205 | 2.8 | Ex. 208 | 4.0 |
| (7) Enzymatically Treated HSP | Comp. Ex. 384 | 1.3 | Comp. Ex. 391 | 1.7 | Comp. Ex. 398 | 2.1 |
| (8) Dispersed HPT | Comp. Ex. 385 | 1.3 | Comp. Ex. 392 | 1.7 | Comp. Ex. 399 | 2.3 |
| (9) HPT-7G | Comp. Ex. 386 | 1.0 | Comp. Ex. 393 | 1.2 | Comp. Ex. 400 | 1.3 |
| (10) NGN-7G-βCD Inclusion Compound (Enzyme Method) | Ex. 203 | 2.3 | Ex. 206 | 3.1 | Ex. 209 | 3.9 |
| (11) NGN-7G | Comp. Ex. 387 | 1.0 | Comp. Ex. 394 | 1.1 | Comp. Ex. 401 | 1.5 |

*In the table, (1) to (5) are each an amount 2% by mass in terms of a content of isoquercitrin or a conversion value; (6) to (9) are each an amount 2% by mass in terms of a content of hesperetin-7-glucoside or a conversion value; and (10) and (11) are each an amount 2% by mass in terms of a content of naringenin-7-glucoside or a conversion value.

TABLE 23

| | Evaluations of Lingering Metallic Taste and Lingering Acidic Taste | | | |
|---|---|---|---|---|
| | Rhamnose/ Flavonoid, molar ratio: 1.0 | | Rhamnose/ Flavonoid, molar ratio: 1.2 | |
| (1) IQC-γCD Inclusion Compound (Enzyme Method) | Ex. 210 | 4.6 | Ex. 213 | 4.0 |
| (2) IQC-γCD Inclusion Compound (Dissolution Method) | Ref. Ex. 64 | 2.4 | Ref. Ex. 65 | 2.0 |
| (3) IQC + γCD | Comp. Ex. 402 | 1.6 | Comp. Ex. 409 | 1.4 |
| (4) Enzymatically Treated IQC | Comp. Ex. 403 | 1.7 | Comp. Ex. 410 | 1.4 |

TABLE 23-continued

| | | Evaluations of Lingering Metallic Taste and Lingering Acidic Taste | | | |
|---|---|---|---|---|---|
| | | Rhamnose/ Flavonoid, molar ratio: 1.0 | | Rhamnose/ Flavonoid, molar ratio: 1.2 | |
| (5) IQC | | Comp. Ex. 404 | 1.5 | Comp. Ex. 411 | 1.2 |
| (6) HPT-7G-βCD Inclusion Compound (Enzyme Method) | | Ex. 211 | 4.6 | Ex. 214 | 4.1 |
| (7) Enzymatically Treated HSP | | Comp. Ex. 405 | 2.2 | Comp. Ex. 412 | 1.9 |
| (8) Dispersed HPT | | Comp. Ex. 406 | 2.7 | Comp. Ex. 413 | 2.2 |
| (9) HPT-7G | | Comp. Ex. 407 | 1.4 | Comp. Ex. 414 | 1.3 |
| (10) NGN-7G-βCD Inclusion Compound (Enzyme Method) | | Ex. 212 | 2.4 | Ex. 215 | 4.1 |
| (11) NGN-7G | | Comp. Ex. 408 | 1.6 | Comp. Ex. 415 | 1.4 |

*In the table, (1) to (5) are each an amount 2% by mass in terms of a content of isoquercitrin or a conversion value; (6) to (9) are each an amount 2% by mass in terms of a content of hesperetin-7-glucoside or a conversion value; and (10) and (11) are each an amount 2% by mass in terms of a content of naringenin-7-glucoside or a conversion value.

TABLE 24

| | | Evaluations of Lingering Metallic Taste and Lingering Acidic Taste | | | |
|---|---|---|---|---|---|
| | | Rhamnose/ Flavonoid, molar ratio: 2.0 | | Rhamnose/ Flavonoid, molar ratio: 5.0 | |
| (1) IQC-γCD Inclusion Compound (Enzyme Method) | | Ex. 216 | 3.8 | Ex. 219 | 3.8 |
| (2) IQC-γCD Inclusion Compound (Dissolution Method) | | Ref. Ex. 66 | 1.9 | Ref. Ex. 67 | 1.9 |
| (3) IQC + γCD | | Comp. Ex. 416 | 1.3 | Comp. Ex. 423 | 1.2 |
| (4) Enzymatically Treated IQC | | Comp. Ex. 417 | 1.4 | Comp. Ex. 424 | 1.3 |
| (5) IQC | | Comp. Ex. 418 | 1.1 | Comp. Ex. 425 | 1.1 |
| (6) HPT-7G-βCD Inclusion Compound (Enzyme Method) | | Ex. 217 | 3.8 | Ex. 220 | 3.7 |
| (7) Enzymatically Treated HSP | | Comp. Ex. 419 | 1.8 | Comp. Ex. 426 | 1.8 |
| (8) Dispersed HPT | | Comp. Ex. 420 | 2.1 | Comp. Ex. 427 | 2.0 |
| (9) HPT-7G | | Comp. Ex. 421 | 1.2 | Comp. Ex. 428 | 1.2 |
| (10) NGN-7G-βCD Inclusion Compound (Enzyme Method) | | Ex. 218 | 3.9 | Ex. 221 | 3.9 |
| (11) NGN-7G | | Comp. Ex. 422 | 1.4 | Comp. Ex. 429 | 1.3 |

*In the table, (1) to (5) are each an amount 2% by mass in terms of a content of isoquercitrin or a conversion value; (6) to (9) are each an amount 2% by mass in terms of a content of hesperetin-7-glucoside or a conversion value; and (10) and (11) are each an amount 2% by mass in terms of a content of naringenin-7-glucoside or a conversion value.

TABLE 25

| | | Evaluations of Lingering Metallic Taste and Lingering Acidic Taste | |
|---|---|---|---|
| | | Rhamnose/ Flavonoid, molar ratio: 10.0 | |
| (1) IQC-γCD Inclusion Compound (Enzyme Method) | | Ex. 222 | 3.6 |
| (2) IQC-γCD Inclusion Compound (Dissolution Method) | | Ref. Ex. 68 | 1.8 |
| (3) IQC + γCD | | Comp. Ex. 430 | 1.2 |
| (4) Enzymatically Treated IQC | | Comp. Ex. 431 | 1.3 |
| (5) IQC | | Comp. Ex. 432 | 1.1 |
| (6) HPT-7G-βCD Inclusion Compound (Enzyme Method) | | Ex. 223 | 3.6 |
| (7) Enzymatically Treated HSP | | Comp. Ex. 433 | 1.7 |
| (8) Dispersed HPT | | Comp. Ex. 434 | 1.9 |
| (9) HPT-7G | | Comp. Ex. 435 | 1.1 |
| (10) NGN-7G-βCD Inclusion Compound (Enzyme Method) | | Ex. 224 | 3.8 |
| (11) NGN-7G | | Comp. Ex. 436 | 1.3 |

*In the table, (1) to (5) are each an amount 2% by mass in terms of a content of isoquercitrin or a conversion value; (6) to (9) are each an amount 2% by mass in terms of a content of hesperetin-7-glucoside or a conversion value; and (10) and (11) are each an amount 2% by mass in terms of a content of naringenin-7-glucoside or a conversion value.

As shown in Tables 18 to 25, the lingering metallic taste and/or the lingering acidic taste owned by the flavonoid is improved by adding the isoquercitrin-γ-cyclodextrin inclusion compound, the hesperetin-7-glucoside-β-cyclodextrin inclusion compound, or the naringenin-7-glucoside-β-cyclodextrin inclusion compound each obtained by the enzyme method. In addition, remarkable improvements are observed in a case where a rhamnose was further added, and in particular, favorable results were obtained for those having a molar ratio of a rhamnose to a flavonoid (rhamnose/flavonoid) of from 0.8 to 1.2. Here, although not indicated in the tables, the similar effects were confirmed for an acidic beverage of which flavonoid content or a conversion amount was 0.02% by mass, or for a tablet of which flavonoid content or a conversion amount was 5% by mass. Here, in the sensory evaluation made according to a dissolution method shown in (2), the similar evaluation could be made with an isoquercitrin-cyclodextrin inclusion compound (dissolution method) prepared in Preparation Example 11. In addition, nearly the same evaluation was made even when the molar ratios of the cyclodextrin to the flavonoid (cyclodextrin/flavonoid) of the flavonoid (isoquercitrin, hesperetin-7-glucoside, or naringenin-7-glucoside) inclusion compound (enzyme method) were changed from 1.0 to 3.0.

11. Cosmetic Effects on Skin

Example 231

Cosmetic effects on skin were evaluated by viability to cell death with pseudo-sunlight (manufactured by Oriel) using an isoquercitrin-γ-cyclodextrin inclusion compound of Preparation Example 4 (an isoquercitrin inclusion compound) and a rhamnose.

Specifically, human dermal fibroblasts (manufactured by PromoCell) were subcultured in a 24-well plate using a medium for cells in a proportion of $3\times10^4$ cells/well. Next, the cells were incubated for 24 hours in the presence of a composition containing an isoquercitrin-γ-cyclodextrin inclusion compound in an amount of 0.007% by mass in terms of isoquercitrin content, and a rhamnose in an amount so that a molar ratio of a rhamnose to an isoquercitrin (rhamnose/isoquercitrin) was 0.1, and then exposed to pseudo-sunlight (manufactured by Oriel, solar simulator, solar dose: 10 KJ/m$^2$). After 24 hours, the viability of the cells was analyzed.

The viability of the cells was analyzed as follows. The cells were incubated at 37° C. and 5% $CO_2$ for 1 hour in the presence of Neutral Red (pigment) (The live cells incorporating Neutral Red, thereby making the cells distinguishable from dead cells or damaged cells, and quantifiable). Next, 50% ethanol and a solution of 0.05 M $NaH_2PO_4$ were added to the cells to thereby extract out the pigment from the cells. Thereafter, the absorbance of the cells was measured with a spectrophotometer at 540 nm, and compared to that of the cells unexposed to the light, and shown as viability (%)= (analytical value at 540 nm of the photo-irradiated cells× 100/analytical value at 540 nm of the cells not irradiated with light) in Table 26.

Examples 232 to 250, Comparative Examples 441 to 500, and Reference Examples 71 to 77

The evaluation was made in the same manner as in Example 231 except that the composition used during the incubation for 24 hours was changed to have the components as listed in Tables 26 to 29.

The details of the components listed in Tables 26 to 29 are the same as those of Tables 1 to 9.

TABLE 26

| | Cosmetic Effects on Skin | | | | | |
|---|---|---|---|---|---|---|
| | Rhamnose Without Addition | | Rhamnose/ Flavonoid, molar ratio: 0.1 | | Rhamnose/ Flavonoid, molar ratio: 0.8 | |
| (1) IQC-γCD Inclusion Compound (Enzyme Method) | Comp. Ex. 441 | 49 | Ex. 231 | 73 | Ex. 234 | 82 |
| (2) IQC-γCD Inclusion Compound (Dissolution Method) | Comp. Ex. 442 | 40 | Ref. Ex. 71 | 45 | Ref. Ex. 72 | 51 |
| (3) IQC + γCD | Comp. Ex. 443 | 35 | Comp. Ex. 452 | 40 | Comp. Ex. 459 | 45 |
| (4) Enzymatically Treated IQC | Comp. Ex. 444 | 35 | Comp. Ex. 453 | 40 | Comp. Ex. 460 | 41 |
| (5) IQC | Comp. Ex. 445 | 30 | Comp. Ex. 454 | 35 | Comp. Ex. 461 | 42 |
| (6) HPT-7G-βCD Inclusion Compound (Enzyme Method) | Comp. Ex. 446 | 45 | Ex. 232 | 50 | Ex. 235 | 82 |
| (7) Enzymatically Treated HSP | Comp. Ex. 447 | 40 | Comp. Ex. 455 | 45 | Comp. Ex. 462 | 51 |
| (8) Dispersed HPT | Comp. Ex. 448 | 35 | Comp. Ex. 456 | 36 | Comp. Ex. 463 | 38 |
| (9) HPT-7G | Comp. Ex. 449 | 30 | Comp. Ex. 457 | 35 | Comp. Ex. 464 | 37 |
| (10) NGN-7G-βCD Inclusion Compound (Enzyme Method) | Comp. Ex. 450 | 45 | Ex. 233 | 55 | Ex. 236 | 78 |
| (11) NGN-7G | Comp. Ex. 451 | 25 | Comp. Ex. 458 | 30 | Comp. Ex. 465 | 34 |

*In the table, (1) to (5) are each an amount 0.007% by mass in terms of a content of isoquercitrin or a conversion value; (6) to (9) are each an amount 0.007% by mass in terms of a content of hesperetin-7-glucoside or a conversion value; and (10) and (11) are each an amount 0.007% by mass in terms of a content of naringenin-7-glucoside or a conversion value.

TABLE 27

| | | Cosmetic Effects on Skin | | |
|---|---|---|---|---|
| | | Rhamnose/ Flavonoid, molar ratio: 1.0 | | Rhamnose/ Flavonoid, molar ratio: 1.2 |
| (1) IQC-γCD Inclusion Compound (Enzyme Method) | Ex. 237 | 95 | Ex. 240 | 92 |
| (2) IQC-γCD Inclusion Compound (Dissolution Method) | Ref. Ex. 73 | 55 | Ref. Ex. 74 | 51 |
| (3) IQC + γCD | Comp. Ex. 466 | 50 | Comp. Ex. 473 | 45 |
| (4) Enzymatically Treated IQC | Comp. Ex. 467 | 50 | Comp. Ex. 474 | 45 |
| (5) IQC | Comp. Ex. 468 | 45 | Comp. Ex. 475 | 42 |
| (6) HPT-7G-βCD Inclusion Compound (Enzyme Method) | Ex. 238 | 89 | Ex. 241 | 85 |
| (7) Enzymatically Treated HSP | Comp. Ex. 469 | 55 | Comp. Ex. 476 | 52 |
| (8) Dispersed HPT | Comp. Ex. 470 | 39 | Comp. Ex. 477 | 36 |
| (9) HPT-7G | Comp. Ex. 471 | 38 | Comp. Ex. 478 | 37 |
| (10) NGN-7G-βCD Inclusion Compound (Enzyme Method) | Ex. 239 | 88 | Ex. 242 | 75 |
| (11) NGN-7G | Comp. Ex. 472 | 35 | Comp. Ex. 479 | 32 |

*In the table, (1) to (5) are each an amount 0.007% by mass in terms of a content of isoquercitrin or a conversion value; (6) to (9) are each an amount 0.007% by mass in terms of a content of hesperetin-7-glucoside or a conversion value; and (10) and (11) are each an amount 0.007% by mass in terms of a content of naringenin-7-glucoside or a conversion value.

TABLE 28

| | | Cosmetic Effects on Skin | | |
|---|---|---|---|---|
| | | Rhamnose/ Flavonoid, molar ratio: 2.0 | | Rhamnose/ Flavonoid, molar ratio: 5.0 |
| (1) IQC-γCD Inclusion Compound (Enzyme Method) | Ex. 243 | 85 | Ex. 246 | 80 |
| (2) IQC-γCD Inclusion Compound (Dissolution Method) | Ref. Ex. 75 | 45 | Ref. Ex. 76 | 44 |
| (3) IQC + γCD | Comp. Ex. 480 | 40 | Comp. Ex. 487 | 39 |
| (4) Enzymatically Treated IQC | Comp. Ex. 481 | 40 | Comp. Ex. 488 | 39 |
| (5) IQC | Comp. Ex. 482 | 35 | Comp. Ex. 489 | 34 |
| (6) HPT-7G-βCD Inclusion Compound (Enzyme Method) | Ex. 244 | 80 | Ex. 247 | 75 |
| (7) Enzymatically Treated HSP | Comp. Ex. 483 | 42 | Comp. Ex. 490 | 40 |
| (8) Dispersed HPT | Comp. Ex. 484 | 36 | Comp. Ex. 491 | 36 |
| (9) HPT-7G | Comp. Ex. 485 | 36 | Comp. Ex. 492 | 35 |
| (10) NGN-7G-βCD Inclusion Compound (Enzyme Method) | Ex. 245 | 73 | Ex. 248 | 72 |
| (11) NGN-7G | Comp. Ex. 486 | 31 | Comp. Ex. 493 | 30 |

*In the table, (1) to (5) are each an amount 0.007% by mass in terms of a content of isoquercitrin or a conversion value; (6) to (9) are each an amount 0.007% by mass in terms of a content of hesperetin-7-glucoside or a conversion value; and (10) and (11) are each an amount 0.007% by mass in terms of a content of naringenin-7-glucoside or a conversion value.

TABLE 29

| | | Cosmetic Effects on Skin |
|---|---|---|
| | | Rhamnose/ Flavonoid, molar ratio: 10.0 |
| (1) IQC-γCD Inclusion Compound (Enzyme Method) | Ex. 249 | 75 |
| (2) IQC-γCD Inclusion Compound (Dissolution Method) | Ref. Ex. 77 | 45 |
| (3) IQC + γCD | Comp. Ex. 494 | 40 |
| (4) Enzymatically Treated IQC | Comp. Ex. 495 | 30 |
| (5) IQC | Comp. Ex. 496 | 35 |
| (6) HPT-7G-βCD Inclusion Compound (Enzyme Method) | Ex. 250 | 70 |
| (7) Enzymatically Treated HSP | Comp. Ex. 497 | 40 |
| (8) Dispersed HPT | Comp. Ex. 498 | 34 |
| (9) HPT-7G | Comp. Ex. 499 | 35 |
| (10) NGN-7G-βCD Inclusion Compound (Enzyme Method) | Ex. 254 | 70 |
| (11) NGN-7G | Comp. Ex. 500 | 30 |

*In the table, (1) to (5) are each an amount 0.007% by mass in terms of a content of isoquercitrin or a conversion value; (6) to (9) are each an amount 0.007% by mass in terms of a content of hesperetin-7-glucoside or a conversion value; and (10) and (11) are each an amount 0.007% by mass in terms of a content of naringenin-7-glucoside or a conversion value.

As shown in Tables 26 to 29, the isoquercitrin-γ-cyclodextrin inclusion compound of Preparation Example 4 at a molar ratio of rhamnose/(isoquercitrin in the isoquercitrin inclusion compound) of from 0.1 to 10.0 showed a high viability against the ultraviolet-inducible cell death of human dermal fibroblasts in the comparisons of other components of the same kind ((2) to (5)). The viability was the highest at a molar ratio of from 0.8 to 1.2. Although not indicated in the tables, the viability of the case of the addition of the rhamnose alone at the same concentration in all the cases was about 5%, and the viability was nearly 0% in the case of no additions of the isoquercitrin inclusion compound and the rhamnose. In addition, when the isoquercitrin was contained in an amount of 0.02% in the isoquercitrin inclusion compound, the viability was increased by about 5%, as compared to that when isoquercitrin was added in an amount of 0.007%, and the same effects were exhibited also when human epidermal keratinocytes (manufactured by TAKARA BIO, INC.) were used. In view of the above, it could be seen that the combination of rhamnose/isoquercitrin inclusion compound protects skin cells against sunlight, and enhances reproducing strength, thereby increasing the viability, reducing the occurrences of wrinkles, and increasing cosmetic effects such as skin complexions. In addition, the hesperetin-7-glucoside-β-cyclodextrin inclusion compound of Preparation Example 6 and the naringenin-7-glucoside-β-cyclodextrin inclusion compound of Preparation Example 7 showed the highest viability in the inclusion compound at a molar ratio of a rhamnose/(a flavonoid in the flavonoid inclusion compound) of from 0.8 to 1.2, in the comparisons of the components of the same kinds ((6) to (9), and (10) to (11)). Here, in the sensory evaluation made according to a dissolution method shown in (2), the same evaluation was made with an isoquercitrin-cyclodextrin inclusion compound (dissolution method) prepared in Preparation Example 11. In addition, nearly the same evaluation was made even when the molar ratios of the cyclodextrin to the flavonoid (cyclodextrin/flavonoid) in the flavonoid (isoquercitrin, hesperetin-7-glucoside, or naringenin-7-glucoside) inclusion compound (enzyme method) were changed from 1.0 to 3.0.

Formulation Examples of Flavonoid Inclusion Compounds

Formulation Example 1: Gummy Candy

A gummy candy containing a dry product of an isoquercitrin-γ-cyclodextrin inclusion compound of Preparation Example 4 was prepared. The present product can be suitably utilized as a food (gummy candy) in which bitterness originated from isoquercitrin was reduced by adding an isoquercitrin-γ-cyclodextrin inclusion compound of Preparation Example 4 and sorbitol.

| Component | % by mass |
| --- | --- |
| Compound of Prep. Ex. 4 | 0.03 |
| Sorbitol | 60.0 |
| Reduced Glucose Syrup | 12.0 |
| Gum Arabic | 5.0 |
| Ion-Exchanged Water | 5.0 |
| Gelatin | 5.0 |
| Colorants | 0.2 |
| Flavors | 0.8 |
| Ion-Exchanged Water | Balance |
| Total | 100.0 |

Formulation Example 2: Chewing Gum

Chewing gum containing a dry product of a hesperetin-7-glucoside-β-cyclodextrin inclusion compound of Preparation Example 6 was prepared. The present product can be suitably utilized as a food (chewing gum) in which bitterness originated from hesperetin-7-glucoside was reduced by adding a hesperetin-7-glucoside-β-cyclodextrin inclusion compound of Preparation Example 6 and a *Stevia* extract.

| Component | % by mass |
| --- | --- |
| Compound of Prep. Ex. 6 | 0.05 |
| Stevia Extract | 0.1 |
| Gum Base | 20.0 |
| Calcium Carbonate | 2.0 |
| Flavors | 1.0 |
| Lactose | Balance |
| Total | 100.00 |

Formulation Example 3: Refreshing Beverage

A refreshing beverage containing a composition containing an isoquercitrin-γ-cyclodextrin inclusion compound of Preparation Example 8 was prepared. The present product can be suitably used as foods (refreshing beverages) in which a lingering metallic taste and a lingering acidic taste originated from the isoquercitrin were reduced, and a lingering sweet taste of the sucralose was reduced by adding a composition containing an isoquercitrin-γ-cyclodextrin inclusion compound of Preparation Example 8.

| Component | % by mass |
| --- | --- |
| Composition of Prep. Ex. 8 | 0.03 |
| Sucralose | 0.04 |
| Citric Acid | 0.2 |
| Trisodium Citrate | 0.06 |
| Flavors | 0.2 |
| Pigment | 0.1 |
| Water | Balance |
| Total | 100.00 |

Formulation Example 4: Jelly (Coffee-Containing Jelly)

A coffee-containing jelly containing a dry product of a composition containing a naringenin-7-glucoside-β-cyclodextrin inclusion compound of Preparation Example 10 was prepared. The present product can be suitably used as a food (coffee-containing jelly) in which bitterness originated from caffeine was reduced by adding a dry product of a composition containing a naringenin-7-glucoside-β-cyclodextrin inclusion compound of Preparation Example 10.

| Component | % by mass |
| --- | --- |
| Composition of Prep. Ex. 10 | 0.1 |
| Caffeine | 0.05% |
| Granulated Sugar | 15.0 |
| Gelatin | 1.0 |
| Coffee Extract | 5.0 |
| Water | Balance |
| Total | 100.0 |

Formulation Example 5: Mouthwash Solution

A mouthwash solution containing a dry product of a composition containing a hesperetin-7-glucoside-β-cyclodextrin inclusion compound of Preparation Example 9 was prepared. The present product can be suitably used as cosmetics (mouthwash solution) in which changes in color tones were small by adding a dry product of a composition containing a hesperetin-7-glucoside-β-cyclodextrin inclusion compound of Preparation Example 9 and erythritol.

| Component | % by mass |
| --- | --- |
| Composition of Prep. Ex. 9 | 0.02 |
| Erythritol | 5.0 |
| Sodium Laurylsulfate | 0.8 |
| Glycerol | 7.0 |
| Ethyl Alcohol | 15.0 |
| 1-Menthol | 0.05 |
| Flavors | 0.04 |
| Water | Balance |
| Total | 100.0 |

Formulation Example 6: Emollient Cream

An emollient cream containing a dry product of a composition containing an isoquercitrin-γ-cyclodextrin inclusion compound containing a rhamnose of Preparation Example 8 was prepared. The present product can be suitably used as cosmetics (emollient cream) in which changes in color tones were small and occurrences of wrinkles were reduced by adding a dry product of a composition containing an isoquercitrin-γ-cyclodextrin inclusion compound containing a rhamnose of Preparation Example 8 and ascorbic acid.

| Component | % by mass |
| --- | --- |
| Composition of Prep. Ex. 8 | 0.6 |
| Ascorbic Acid | 0.1 |
| Beeswax | 0.2 |
| Stearyl Alcohol | 5.0 |
| Stearic Acid | 8.0 |
| Squalane | 10.0 |
| Self-Emulsifiable Propylene Glycol Monostearate | 3.0 |
| Polyoxyethylene Cetyl Ether (20 EO) | 1.0 |
| Perfumes | 0.5 |
| Preservative | Trace |
| Propylene Glycol | 4.8 |
| Glycerol | 3.0 |
| Sodium Hyaluronate | 0.1 |
| Triethanolamine | 1.0 |
| Purified Water | Balance |
| Total | 100.0 |

Formulation Example 7: Emollient Lotion

An emollient cream containing a dry product of a composition containing a hesperetin-7-glucoside-β-cyclodextrin inclusion compound of Preparation Example 9 was prepared. The present product can be suitably used as cosmetics (emollient lotion) in which changes in color tones were small by adding a dry product of a composition containing a hesperetin-7-glucoside-β-cyclodextrin inclusion compound of Preparation Example 9 and erythritol.

| Component | % by mass |
| --- | --- |
| Composition of Prep. Ex. 9 | 0.05 |
| Erythritol | 5.0 |
| Stearic Acid | 2.0 |
| Cetanol | 1.5 |
| Vaseline | 3.0 |
| Lanolin Alcohol | 2.0 |
| Liquid Paraffin | 10.0 |
| Polyoxyethylene Monooleic Acid Ester (10 EO) | 2.0 |
| Perfumes | 0.5 |
| Preservative | Trace |
| Propylene Glycol | 4.8 |
| Glycerol | 3.0 |
| Sodium Hyaluronate | 0.1 |
| Triethanolamine | 1.0 |
| Purified Water | Balance |
| Total | 100.0 |

Formulation Example 8: Dentifrice

A dentifrice containing a dry product of a composition containing a naringenin-7-glucoside-β-cyclodextrin inclusion compound of Preparation Example 10 was prepared. The present product can be suitably used as cosmetics (dentifrice) in which changes in color tones were small by adding a dry product of a composition containing a naringenin-7-glucoside-β-cyclodextrin inclusion compound of Preparation Example 10 and xylitol.

| Component | % by mass |
| --- | --- |
| Composition of Prep. Ex. 10 | 0.1 |
| Xylitol | 1.0 |
| Calcium Hydrogen Phosphate | 42.0 |
| Glycerol | 18.0 |
| Carrageenan | 0.9 |
| Sodium Laurylsulfate | 1.2 |
| Butyl Paraoxybenzoate | 0.005 |
| Flavors | 1.0 |
| Water | Balance |
| Total | 100.0 |

Formulation Example 9: Ice Cream

An ice cream containing a dry product of a composition containing a hesperetin-7-glucoside-β-cyclodextrin inclusion compound of Preparation Example 9 was prepared. The present product can be suitably used as a food (ice cream) in which acridity originated from chlorogenic acid was small by adding a dry product of a composition containing a hesperetin-7-glucoside-β-cyclodextrin inclusion compound of Preparation Example 9.

| Component | % by mass |
| --- | --- |
| Composition of Prep. Ex. 9 | 0.05 |
| Chlorogenic Acid | 0.05 |
| Heavy Cream (45% Fat) | 33.8 |
| Powdered Skim Milk | 11.0 |
| Granulated Sugar | 14.8 |
| Sugared Egg Yolk | 0.3 |
| Vanilla Essence | 0.1 |
| Water | Balance |
| Total | 100.0 |

Formulation Example 10: Tablet

A tablet containing a dry product of a composition containing an isoquercitrin-γ-cyclodextrin inclusion compound of Preparation Example 8 was prepared. The present product can be suitably used as a food (tablet) in which sweetness originated from erythritol was improved by adding a dry product of a composition containing an isoquercitrin-γ-cyclodextrin inclusion compound of Preparation Example 8.

| Component | % by mass |
| --- | --- |
| Composition of Prep. Ex. 8 | 20.0 |
| Crystalline Cellulose | 10.0 |
| Reduced Maltose Glucose Syrup Powder | 6.0 |
| Calcium Stearate | 2.0 |
| Shellac | 2.0 |
| Erythritol | 60.0 |
| Total | 100.0 |

INDUSTRIAL APPLICABILITY

According to the present invention, the bitterness and the changes in color tones originated from flavonoids can be inhibited, and foodstuff or the like having an unpleasant taste can be improved, so that the present invention can be suitably utilized in fields such as medicaments, foodstuff, health foods, foods for specified health use, and cosmetics.

The invention claimed is:

1. A composition comprising:
one or more material selected from the group consisting of fatty acids, proteins, peptides, amino acids, vitamins, minerals, alcohols, sweeteners, acidulants, antioxidants, thickening stabilizers, and surfactants; and
a flavonoid-cyclodextrin inclusion compound,
wherein the inclusion compound comprises an inclusion compound obtained by treating a flavonoid having a rhamnoside structure with an enzyme having rhamnosidase activity and glucosidase activity under reaction conditions of a pH of from 3 to 7 in the presence of a cyclodextrin,
wherein the cyclodextrin comprises one or more selected from the group consisting of β-cyclodextrin, and γ-cyclodextrin, and
wherein the flavonoid in the inclusion compound comprises one or more selected from the group consisting of isoquercitrin, hesperetin-7-glucoside, naringenin-7-glucoside (prunin), diosmetin-7-glucoside, eriodictyol-7-glucoside, luteolin-7-glucoside, delphinidin-3-glucoside, cyanidin-3-glucoside, isorhamnetin-3-glucoside, kaempferol-3-glucoside, apigenin-7-glucoside, acacetin-7-glucoside, and derivatives thereof.

2. The composition according to claim 1, wherein the material comprises one or more selected from the group consisting of vitamins, sugar alcohols, high-intensity sweeteners, sugars, and antioxidants.

3. The composition according to claim 1, wherein the material comprises one or more selected from the group consisting of ascorbic acid, sorbitol, erythritol, xylitol, aspartame, sucralose, acesulfame potassium, *stevia* extracts, tea extracts, catechin, tannin, caffeine, chlorogenic acid, and rhamnose.

4. The composition according to claim 1, wherein the material comprises one or more selected from the group consisting of aspartame, sucralose, acesulfame potassium, and *stevia* extracts.

5. The composition according to claim 1, wherein the material comprises one or more selected from the group consisting of ascorbic acid, sorbitol, erythritol, xylitol, and rhamnose.

6. The composition according to claim 1, wherein the material comprises one or more selected from the group consisting of tea extracts, catechin, tannin, caffeine, and chlorogenic acid.

7. The composition according to claim 1, wherein a content of the material is from 0.001 to 80% by mass of the composition.

8. The composition according to claim 1, wherein a molar ratio of cyclodextrin to flavonoid (cyclodextrin/flavonoid) in the inclusion compound is from 1.0 to 3.0.

9. The composition according to claim 1, wherein the inclusion compound comprises one or more selected from the group consisting of isoquercitrin-γ-cyclodextrin, hesperetin-7-glucoside-β-cyclodextrin, and naringenin-7-glucoside-β-cyclodextrin, wherein a molar ratio of cyclodextrin to flavonoid (cyclodextrin/flavonoid) in the inclusion compound is from 1.0 to 1.8.

10. The composition according to claim 1, wherein the inclusion compound comprises isoquercitrin-γ-cyclodextrin.

11. The composition according to claim 1, wherein a content of the inclusion compound, in terms of a flavonoid content, is from 0.001 to 10% by mass of the composition.

12. The composition according to claim 1, further comprising a rhamnose, wherein a molar ratio of rhamnose to flavonoid (rhamnose/flavonoid) in the inclusion compound is from 0.1 to 10.

13. The composition according to claim 12, wherein the molar ratio of rhamnose to flavonoid (rhamnose/flavonoid) in the inclusion compound is from 0.8 to 1.2.

14. Foodstuff comprising a composition as defined in claim 1.

15. A medicament comprising a composition as defined in claim 1.

16. Cosmetics comprising a composition as defined in claim 1.

17. A method for producing foodstuff, a medicament, or cosmetics, comprising mixing foodstuff raw materials, medicament raw materials, or cosmetic raw materials with a composition as defined in claim 1.

18. A method for inhibiting bitterness originated from a flavonoid in foodstuff or a medicament, comprising mixing foodstuff raw materials or medicament raw materials with a composition as defined in claim 1.

19. A method for inhibiting an unpleasant taste in foodstuff or a medicament, comprising mixing foodstuff raw materials or medicament raw materials with a composition as defined in claim 1.

20. The method for inhibiting an unpleasant taste according to claim 19, wherein the unpleasant taste is lingering sweet taste, sweetness, bitterness, acerbity, acridity, or acidity originated from the material.

21. A method for inhibiting changes in color tones originated from a flavonoid in foodstuff, a medicament, or cosmetics, comprising mixing foodstuff raw materials, medicament raw materials, or cosmetic raw materials with a composition as defined in claim 1.

* * * * *